US006214790B1

(12) United States Patent
Richelson et al.

(10) Patent No.: US 6,214,790 B1
(45) Date of Patent: Apr. 10, 2001

(54) NEO-TRYPTOPHAN

(75) Inventors: Elliott Richelson, Ponte Vedra Beach; Bernadette Marie Cusack, Jacksonville, both of FL (US); Yuan-Ping Pang; Daniel J. McCormick, both of Rochester, MN (US); Abdul Fauq, Jacksonville, FL (US); Beth Marie Tyler, Neptune Beach, FL (US); Mona Boules, Jacksonville, FL (US)

(73) Assignee: Mayo Foundation for Medical Education And Research, Rochester, MN (US)

( * ) Notice: Subject to any disclaimer, the term of this patent is extended or adjusted under 35 U.S.C. 154(b) by 0 days.

(21) Appl. No.: 09/289,693

(22) Filed: Apr. 9, 1999

Related U.S. Application Data
(60) Provisional application No. 60/112,137, filed on Dec. 14, 1998, provisional application No. 60/098,119, filed on Aug. 27, 1998, provisional application No. 60/092,195, filed on Jul. 9, 1998, and provisional application No. 60/081,356, filed on Apr. 10, 1998.

(51) Int. Cl.[7] .................... A61K 31/405; A61K 38/02; C07D 209/08; C07K 2/00; C12Q 1/37
(52) U.S. Cl. ................... 514/2; 435/23; 514/14; 514/415; 530/300; 530/327; 548/469; 548/503; 548/508; 548/509; 548/510
(58) Field of Search ................... 530/300, 327; 548/469, 503, 508, 509, 510; 514/2, 14, 415; 435/23, 24

(56) References Cited

U.S. PATENT DOCUMENTS

| | | | |
|---|---|---|---|
| 4,299,838 | 11/1981 | Durlach | 424/274 |
| 4,331,646 | 5/1982 | Delaage | 424/1 |
| 4,518,587 | 5/1985 | Laruelle et al. | 514/19 |
| 5,393,740 | 2/1995 | Amagaya et al. | 514/17 |
| 5,631,265 | 5/1997 | Audia et al. | 514/292 |
| 6,046,180 | * 4/2000 | Jackson et al. | 514/75 |

FOREIGN PATENT DOCUMENTS

| | | |
|---|---|---|
| 0 333 071 A2 | 9/1989 | (EP) . |
| WO 96/03400 | 2/1996 | (WO) . |
| WO 96/39162 | 12/1996 | (WO) . |
| WO 97/48400 | 12/1997 | (WO) . |

OTHER PUBLICATIONS

Al–Rodhan NR et al., Structure–antinociceptive activity of neurotensin and some novel analogues in the periaqueductal gray region of the brainstem, *Brain Res.* 557: 227–235 (1991).

Bissette G et al., Hypothermia and intolerance to cold induced by intracisternal administration of the hypothalamic peptide neurotensin, *Nature* 262:607–609 (1976).

Carraway R and SE Leeman, The isolation of a new hypotensive peptide, neurotensin, from bovine hypothalami, *J. Biol. Chem.* 248: 6854–6861 (1973).

(List continued on next page.)

*Primary Examiner*—Jeffrey E. Russel
(74) *Attorney, Agent, or Firm*—Fish & Richardson P.C., P.A.

(57) ABSTRACT

The invention provides a novel amino acid, neo-tryptophan, as well as polypeptides containing this novel amino acid such as neurotensin analogs. In addition, the invention provides neo-tryptophan derivatives, serotonin-like neo-tryptophan derivatives, and polypeptides containing such derivatives. The invention also provides methods for making neo-tryptophan, neo-tryptophan derivatives, serotonin-like neo-tryptophan derivatives, and compositions containing these compounds. Further, the invention provides methods for inducing a neurotensin response in a mammal as well as methods for treating a mammal having a serotonin recognition molecule.

66 Claims, 5 Drawing Sheets

OTHER PUBLICATIONS

Clineschmidt BV and JC McGuffin, Neurotensin administered intracisternally inhibits responsiveness of mice to noxious stimuli, *Eur. J. Pharmacol.* 46: 395–396 (1977).

Cusack B et al., Pharamcological and biochemical profiles of unique neurotensin 8–13 analogs exhibiting species selectivity, stereoselectivity, and superagonism, *J. Biol. Chem.* 270: 18359–18366 (1995).

Cusack B et al., Pharmacological studies on novel neurotensin mimetics: discovery of a pharmacologically unique agent exhibiting concentration–dependent dual effects as antagonist and agonist, *Mol. Pharmacol.* 44:1036–1040 (1993).

Fauq AH et al., Synthesis of (2S)–2–amino–3–(1H–4–indolyl) propanoic acid, a novel tryptophan analog for structural modification of bioactive peptides, *Tetrahedron: Asymmetry* 9:4127–4134 (1998).

Huang W and Hanson GR, Differential effect of haloperidol on release of neurotensin in extrapyramidal and limbic systems, *Eur. J. Pharmacology* 332:15–21 (1997).

Jolicoeur FB et al., Differential neurobehavioral effects of neurotensin and structural analogues, *Peptides* 2:171–175 (1981).

Kitabgi P et al., Neurotensin binding to extraneural and neural receptors: comparison with biological activity and structure–activity relationships, *Molecular Pharmacology* 18:11–19 (1980).

Lambert PD et al., Anatomy and mechanisms of neurotensin–dopamine interactions in the central nervous system, *Annals New York Academy of Sci.* 757:377–389 (1995).

Li X–M et al., Neurotensin peptides antagonistically regulate postsynaptic dopamine D2 receptors in rat nucleus accumbens: a receptor binding and microdialysis study, J. Neural. Transm. 102:125–137 (1995).

Morbeck DE et al., Analysis of hormone–receptor interaction sites using synthetic peptides: Receptor binding regions of the alpha–subunit of human choriogonadotropin, In: Methods: *A Companion to Methods in Enzymology* 5:191–200, Academic Press Inc., New York (1993).

Radke JM et al., Atypical antipsychotic drugs selectively increase neurotensin efflux in dopamine terminal regions, Proc. Natl. Acad. Sci. USA 95:11462–11464 (1998).

Sarhan S et al., Comparative antipsychotic profiles of neurotensin and a related systemically active peptide agonist, *Peptides* 18(8):1223–1227 (1997).

Snijders R et al., Neurotensin induces catalepsy in mice, *Neuropharmacology* 21: 465–468 (1982).

Troxler von Franz, Praparative verwendung von mannich-–basen von hydroxy–indolen als alkylierungsmittel, Helvetica Chimica Acta, Volumen 51, Fasciculus 6:1214–1224 (1968) (Summary in English only).

Tyler BM et al., In vitro binding and CNS effects of novel neurotensin agonists that cross the blood–brain barrier, Neuropharmacology 38:1027–1034 (1999).

Vincent Jean–Pierre et al., Neurotensin and neurotensin receptors, TIPS 20:302–309 (1999).

* cited by examiner

FIG. 3 Synthesis of (DL)-Neo-Tryptophan

SEQUENCE LISTING

<160> NUMBER OF SEQ ID NOS: 30

<210> SEQ ID NO 1
<211> LENGTH: 13
<212> TYPE: PRT
<213> ORGANISM: Artificial Sequence
<220> FEATURE:

```
<223> OTHER INFORMATION: Synthetically generated peptide
<220> FEATURE:
<221> NAME/KEY: SITE
<222> LOCATION: (1)...(1)
<223> OTHER INFORMATION: Xaa = pyrrolidone carboxylic acid

<400> SEQUENCE: 1

Xaa Leu Tyr Glu Asn Lys Pro Arg Arg Pro Tyr Ile Leu
 1               5                  10

<210> SEQ ID NO 2
<211> LENGTH: 6
<212> TYPE: PRT
<213> ORGANISM: Artificial Sequence
<220> FEATURE:
<223> OTHER INFORMATION: Synthetically generated peptide

<400> SEQUENCE: 2

Arg Arg Pro Tyr Ile Leu
 1               5

<210> SEQ ID NO 3
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 3

Arg Pro Tyr Ile Leu
 1               5

<210> SEQ ID NO 4
<211> LENGTH: 6
<212> TYPE: PRT
<213> ORGANISM: Artificial Sequence
<220> FEATURE:
<223> OTHER INFORMATION: Synthetically generated peptide

<400> SEQUENCE: 4

Arg Arg Pro Trp Ile Leu
 1               5

<210> SEQ ID NO 5
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: MUTAGEN
<222> LOCATION: (5)...(5)
<223> OTHER INFORMATION: Xaa = tert-Leu

<400> SEQUENCE: 5

Arg Arg Pro Tyr Xaa Leu
 1               5

<210> SEQ ID NO 6
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: MUTAGEN
<222> LOCATION: (1)...(1)
<223> OTHER INFORMATION: Xaa = N-methyl-Arg
<220> FEATURE:
```

```
<221> NAME/KEY: MUTAGEN
<222> LOCATION: (5)...(5)
<223> OTHER INFORMATION: Xaa = tert-Leu

<400> SEQUENCE: 6

Xaa Lys Pro Trp Xaa Leu
 1               5

<210> SEQ ID NO 7
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: MUTAGEN
<222> LOCATION: (1)...(1)
<223> OTHER INFORMATION: Xaa = D-Lys

<400> SEQUENCE: 7

Xaa Arg Pro Tyr Ile Leu
 1               5

<210> SEQ ID NO 8
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: MUTAGEN
<222> LOCATION: (2)...(2)
<223> OTHER INFORMATION: Xaa = D-ornithine

<400> SEQUENCE: 8

Arg Xaa Pro Tyr Ile Leu
 1               5

<210> SEQ ID NO 9
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: MUTAGEN
<222> LOCATION: (4)...(4)
<223> OTHER INFORMATION: Xaa = L-3,1-Naphthalylalanine

<400> SEQUENCE: 9

Arg Arg Pro Xaa Ile Leu
 1               5

<210> SEQ ID NO 10
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: MUTAGEN
<222> LOCATION: (4)...(4)
<223> OTHER INFORMATION: Xaa = D-neo-Trp

<400> SEQUENCE: 10

Arg Arg Pro Xaa Ile Leu
 1               5

<210> SEQ ID NO 11
```

<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: MUTAGEN
<222> LOCATION: (4)...(4)
<223> OTHER INFORMATION: Xaa = L-neo-Trp

<400> SEQUENCE: 11

Arg Arg Pro Xaa Ile Leu
 1               5

<210> SEQ ID NO 12
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: MUTAGEN
<222> LOCATION: (4)...(4)
<223> OTHER INFORMATION: Xaa = L-neo-Trp
<220> FEATURE:
<221> NAME/KEY: MUTAGEN
<222> LOCATION: (5)...(5)
<223> OTHER INFORMATION: Xaa = tert-Leu

<400> SEQUENCE: 12

Arg Arg Pro Xaa Xaa Leu
 1               5

<210> SEQ ID NO 13
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: MUTAGEN
<222> LOCATION: (1)...(1)
<223> OTHER INFORMATION: Xaa = D-Lys
<220> FEATURE:
<221> NAME/KEY: MUTAGEN
<222> LOCATION: (4)...(4)
<223> OTHER INFORMATION: Xaa = D-neo-Trp
<220> FEATURE:
<221> NAME/KEY: MUTAGEN
<222> LOCATION: (5)...(5)
<223> OTHER INFORMATION: Xaa = tert-Leu

<400> SEQUENCE: 13

Xaa Arg Pro Xaa Xaa Leu
 1               5

<210> SEQ ID NO 14
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: MUTAGEN
<222> LOCATION: (1)...(1)
<223> OTHER INFORMATION: Xaa = D-Lys
<220> FEATURE:
<221> NAME/KEY: MUTAGEN
<222> LOCATION: (4)...(4)
<223> OTHER INFORMATION: Xaa = L-neo-Trp
<220> FEATURE:
<221> NAME/KEY: MUTAGEN
<222> LOCATION: (5)...(5)

<223> OTHER INFORMATION: Xaa = tert-Leu

<400> SEQUENCE: 14

Xaa Arg Pro Xaa Xaa Leu
 1               5

<210> SEQ ID NO 15
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: MUTAGEN
<222> LOCATION: (1)...(1)
<223> OTHER INFORMATION: Xaa = D-Lys
<220> FEATURE:
<221> NAME/KEY: MUTAGEN
<222> LOCATION: (4)...(4)
<223> OTHER INFORMATION: Xaa = L-neo Trp

<400> SEQUENCE: 15

Xaa Arg Pro Xaa Ile Leu
 1               5

<210> SEQ ID NO 16
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: MUTAGEN
<222> LOCATION: (1)...(10)
<223> OTHER INFORMATION: Xaa = N-methyl-Arg
<220> FEATURE:
<221> NAME/KEY: MUTAGEN
<222> LOCATION: (4)...(4)
<223> OTHER INFORMATION: Xaa = L-neo-Trp
<220> FEATURE:
<221> NAME/KEY: MUTAGEN
<222> LOCATION: (5)...(5)
<223> OTHER INFORMATION: Xaa = tert-Leu

<400> SEQUENCE: 16

Xaa Lys Pro Xaa Xaa Leu
 1               5

<210> SEQ ID NO 17
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: MUTAGEN
<222> LOCATION: (1)...(1)
<223> OTHER INFORMATION: Xaa = N-methyl-Arg
<220> FEATURE:
<221> NAME/KEY: MUTAGEN
<222> LOCATION: (4)...(4)
<223> OTHER INFORMATION: Xaa = L-neo-trp
<220> FEATURE:
<221> NAME/KEY: MUTAGEN
<222> LOCATION: (5)...(5)
<223> OTHER INFORMATION: Xaa = tert-Leu

<400> SEQUENCE: 17

Xaa Arg Pro Xaa Xaa Leu
 1               5

```
<210> SEQ ID NO 18
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: MUTAGEN
<222> LOCATION: (1)...(1)
<223> OTHER INFORMATION: Xaa = N-methyl-Arg
<220> FEATURE:
<221> NAME/KEY: MUTAGEN
<222> LOCATION: (2)...(2)
<223> OTHER INFORMATION: Xaa = Diaminobutyric acid
<220> FEATURE:
<221> NAME/KEY: MUTAGEN
<222> LOCATION: (4)...(4)
<223> OTHER INFORMATION: Xaa = L-neo-Trp
<220> FEATURE:
<221> NAME/KEY: MUTAGEN
<222> LOCATION: (5)...(5)
<223> OTHER INFORMATION: Xaa = tert-Leu

<400> SEQUENCE: 18

Xaa Xaa Pro Xaa Xaa Leu
 1               5

<210> SEQ ID NO 19
<211> LENGTH: 5
<212> TYPE: PRT
<213> ORGANISM: Artificial Sequence
<220> FEATURE:
<223> OTHER INFORMATION: Synthetically generated peptide
<220> FEATURE:
<221> NAME/KEY: MUTAGEN
<222> LOCATION: (1)...(1)
<223> OTHER INFORMATION: Xaa = D-Lys
<220> FEATURE:
<221> NAME/KEY: MUTAGEN
<222> LOCATION: (3)...(3)
<223> OTHER INFORMATION: Xaa = L-neo-Trp
<220> FEATURE:
<221> NAME/KEY: MUTAGEN
<222> LOCATION: (4)...(4)
<223> OTHER INFORMATION: Xaa = tert-Leu

<400> SEQUENCE: 19

Xaa Pro Xaa Xaa Leu
 1               5

<210> SEQ ID NO 20
<211> LENGTH: 5
<212> TYPE: PRT
<213> ORGANISM: Artificial Sequence
<220> FEATURE:
<223> OTHER INFORMATION: Synthetically generated peptide
<220> FEATURE:
<221> NAME/KEY: MUTAGEN
<222> LOCATION: (1)...(1)
<223> OTHER INFORMATION: Xaa = D-Lys
<220> FEATURE:
<221> NAME/KEY: MUTAGEN
<222> LOCATION: (3)...(3)
<223> OTHER INFORMATION: Xaa = L-neo-Trp

<400> SEQUENCE: 20

Xaa Pro Xaa Ile Leu
 1               5

<210> SEQ ID NO 21
<211> LENGTH: 5
<212> TYPE: PRT
<213> ORGANISM: Artificial Sequence
```

```
<220> FEATURE:
<223> OTHER INFORMATION: Synthetically generated peptide
<220> FEATURE:
<221> NAME/KEY: MUTAGEN
<222> LOCATION: (1)...(1)
<223> OTHER INFORMATION: Xaa = Diaminobutyric acid
<220> FEATURE:
<221> NAME/KEY: MUTAGEN
<222> LOCATION: (3)...(3)
<223> OTHER INFORMATION: Xaa = L-neo-Trp
<220> FEATURE:
<221> NAME/KEY: MUTAGEN
<222> LOCATION: (4)...(4)
<223> OTHER INFORMATION: Xaa = tert-Leu

<400> SEQUENCE: 21

Xaa Pro Xaa Xaa Leu
 1               5

<210> SEQ ID NO 22
<211> LENGTH: 5
<212> TYPE: PRT
<213> ORGANISM: Artificial Sequence
<220> FEATURE:
<223> OTHER INFORMATION: Synthetically generated peptide
<220> FEATURE:
<221> NAME/KEY: MUTAGEN
<222> LOCATION: (1)...(1)
<223> OTHER INFORMATION: Xaa = Diaminobutyric acid
<220> FEATURE:
<221> NAME/KEY: MUTAGEN
<222> LOCATION: (3)...(3)
<223> OTHER INFORMATION: Xaa = L-neo-Trp

<400> SEQUENCE: 22

Xaa Pro Xaa Ile Leu
 1               5

<210> SEQ ID NO 23
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: MUTAGEN
<222> LOCATION: (2)...(2)
<223> OTHER INFORMATION: Xaa = D-ornithine
<220> FEATURE:
<221> NAME/KEY: MUTAGEN
<222> LOCATION: (4)...(4)
<223> OTHER INFORMATION: Xaa = L-neo-Trp

<400> SEQUENCE: 23

Arg Xaa Pro Xaa Ile Leu
 1               5

<210> SEQ ID NO 24
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: MUTAGEN
<222> LOCATION: (2)...(2)
<223> OTHER INFORMATION: Xaa = D-ornithine
<220> FEATURE:
<221> NAME/KEY: MUTAGEN
<222> LOCATION: (4)...(4)
<223> OTHER INFORMATION: Xaa = L-neo-Trp
<220> FEATURE:
<221> NAME/KEY: MUTAGEN
```

```
<222> LOCATION: (5)...(5)
<223> OTHER INFORMATION: Xaa = tert-Leu

<400> SEQUENCE: 24

Arg Xaa Pro Xaa Xaa Leu
 1               5

<210> SEQ ID NO 25
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 25

Asp Arg Val Tyr Ile His Pro Phe
 1               5

<210> SEQ ID NO 26
<211> LENGTH: 8
<212> TYPE: PRT
<213> ORGANISM: Artificial Sequence
<220> FEATURE:
<223> OTHER INFORMATION: Synthetically generated peptide
<220> FEATURE:
<221> NAME/KEY: MUTAGEN
<222> LOCATION: (4)...(4)
<223> OTHER INFORMATION: Xaa = L-neo-Trp

<400> SEQUENCE: 26

Asp Arg Val Xaa Ile His Pro Phe
 1               5

<210> SEQ ID NO 27
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 27

Arg Pro Pro Gly Phe Ser Pro Phe Arg
 1               5

<210> SEQ ID NO 28
<211> LENGTH: 9
<212> TYPE: PRT
<213> ORGANISM: Artificial Sequence
<220> FEATURE:
<223> OTHER INFORMATION: Synthetically generated peptide
<220> FEATURE:
<221> NAME/KEY: MUTAGEN
<222> LOCATION: (5)...(5)
<223> OTHER INFORMATION: Xaa = L-neo-Trp

<400> SEQUENCE: 28

Arg Pro Pro Gly Xaa Ser Pro Phe Arg
 1               5

<210> SEQ ID NO 29
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 29

Tyr Gly Gly Phe Leu
```

```
                                1                   5

<210> SEQ ID NO 30
<211> LENGTH: 5
<212> TYPE: PRT
<213> ORGANISM: Artificial Sequence
<220> FEATURE:
<223> OTHER INFORMATION: Synthetically generated peptide
<220> FEATURE:
<221> NAME/KEY: MUTAGEN
<222> LOCATION: (1)...(1)
<223> OTHER INFORMATION: Xaa = L-neo-Trp

<400> SEQUENCE: 30

Xaa Gly Gly Phe Leu
 1               5
```

NEO-TRYPTOPHAN

CROSS REFERENCE TO RELATED APPLICATIONS

This application claims priority from the following U.S. Provisional Applications, U.S. Ser. No. 60/081,356, filed Apr. 10, 1998, U.S. Ser. No. 60/092,195, filed Jul. 9, 1998, U.S. Ser. No. 60/098,119, filed Aug. 27, 1998 and U.S. Ser. No. 60/112,137, filed Dec. 14, 1998.

STATEMENT AS TO FEDERALLY SPONSORED RESEARCH

Funding for the work described herein was provided by the federal government, which may have certain rights in the invention.

BACKGROUND

1. Technical Field

The invention relates to a novel amino acid, neo-tryptophan, as well as polypeptides containing this novel amino acid.

2. Background Information

Tryptophan is an essential component in human nutrition since it is not synthesized by the body. In addition, tryptophan is a hydrophobic amino acid that is part of many polypeptides.

Polypeptides as well as many other types of compounds such as neurotransmitters and drugs can exert profound effects on the body. For example, neurotensin (NT) is a tridecapeptide that induces antinociception and hypothermia upon direct administration to brain. Systemic administration of NT does not induce these effects since NT is rapidly degraded by proteases and has poor blood brain barrier permeability. Currently, two NT receptors have been identified and cloned. The first NT receptor is designated NTR1, while the second is designated NTR2. Both NTR1 and NTR2 are G-protein coupled receptors that are expressed by various brain tissues.

Serotonin (5HT) is a neurotransmitter that is essential to brain function. Multiple serotonin receptors and transporters have been identified and cloned. Briefly, de novo synthesis of serotonin from tryptophan occurs in the cytoplasm of a cell. Once synthesized, vesicular monoamine transporters package the transmitter into vesicular compartments so that its release can be regulated. Once released into the synapse upon proper stimulation, the transmitter can bind specific serotonin receptors, can be degraded by specific enzymes, and/or can be transported back into a cell by specific plasma membrane serotonin transporters and then re-packaged into vesicles. Thus, both serotonin receptors and transporters specifically recognize serotonin.

Apomorphine is an example of a drug that also influences brain function. Specifically, apomorphine is a non-selective dopamine $D_2/D_3$ receptor agonist. At low doses, apomorphine (e.g., 25–200 μg/kg) activates pre-synaptic receptors, while at higher doses (e.g., 600 μg/kg) it influences post-synaptic sites. Thus, the behavioral affects of apomorphine vary with dosage. In mice and rats, high doses of apomorphine cause a characteristic climbing behavior as well as oro-facial stereotypies such as sniffing and licking behaviors. Using these high doses of apomorphine, atypical neuroleptic compounds have been identified based on their ability to block potently the climbing behavior while causing little change to the sniffing and licking behaviors. Both typical and atypical neuroleptic compounds have been used to treat schizophrenia and other psychotic disorders. Atypical drugs are preferred because of their lower propensity to cause motor side effects (e.g., extrapyramidal side effects such as parkinsonism and tardive dyskinesia).

SUMMARY

The invention provides a novel amino acid, neo-tryptophan, as well as polypeptides containing neo-tryptophan. In addition, the invention provides neo-tryptophan derivatives and serotonin-like neo-tryptophan derivatives as well as compositions containing these derivatives. Specifically, the invention provides neurotensin (NT) polypeptide analogs as well as other polypeptides that contain neo-tryptophan. The invention also provides methods for making neo-tryptophan, neo-tryptophan derivatives, serotonin-like neo-tryptophan derivatives, and compositions containing such compounds. Further, the invention provides methods for inducing a neurotensin response in a mammal as well as methods for treating a mammal having a serotonin recognition molecule.

One aspect of the invention features a polypeptide containing neo-tryptophan. The polypeptide can be substantially pure, and neo-tryptophan can be L-neo-tryptophan or D-neo-tryptophan. The polypeptide can interact with a neurotensin receptor, and can be a neurotensin analog with neo-tryptophan being located at amino acid position 11 of neurotensin. The polypeptide can be NT64D, NT64L, NT65L, NT66D, NT66L, NT67L, NT69L, NT69L', NT71, NT72, NT73, NT74, NT75, NT76, NT77, Ang1, Brdy1, or Lenk1.

In another aspect, the invention features an amino acid that is neo-tryptophan. The amino acid can be substantially pure, and can be L-neo-tryptophan or D-neo-tryptophan.

Another aspect of the invention features a neo-tryptophan derivative. The neo-tryptophan derivative can contain neo-tryptophan and a blocking group (e.g., Fmoc or Boc).

Another aspect of the invention features a serotonin-like neo-tryptophan derivative having the following structure:

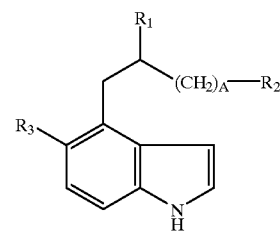

with $R_1$, $R_2$, and $R_3$ being H, OH, $CH_3$, SH, F, $NH_2$, or COOH, and A being zero, one, two, or three. For example, $R_1$ and $R_3$ each can be a hydroxyl group, $R_2$ can be an amino group, and A can be zero.

Another aspect of the invention features a method of synthesizing neo-tryptophan. The method includes providing 4-hydroxymethyl indole, and substituting the hydroxyl group of the 4-hydroxymethyl indole with a glycyl unit to produce neo-tryptophan. The N-1 nitrogen of the 4-hydroxymethyl indole can be protected by a protecting group (e.g., Boc) that can be removed after the substitution. The method can include (a) providing 2-methyl-3-nitrobenzoic acid, (b) esterifying the 2-methyl-3-nitrobenzoic acid to form an esterification product, (c) reacting the esterification product with N,N-dimethylformamide dimethylacetal to produce an enamine product, (d) performing reductive cyclization on the enamine product to produce a 4-substituted indole methyl ester, (e) protecting the indole nitrogen of the 4-substituted indole methyl ester with a Boc group, (f) reducing the protected 4-substituted indole methyl ester with DIBAL to produce N-Boc-4-hydroxymethyl indole, (g) converting the N-Boc-4-hydroxymethyl indole into benzylic bromide, (h) performing $SN_2$ displacement of the bromide of the benzylic bromide with a carbanion to produce diastereomeric bislactim products, (i) isolating one of the diastereomeric bislactim products, (j) hydrolyzing the isolated diastereomeric bislactim product to produce an aminoester product, (k) saponifying the aminoester product to produce an $N^{ind}$-t-Boc amino acid, and (l) removing the Boc group to produce neo-tryptophan.

Another aspect of the invention features a method of synthesizing a neo-tryptophan derivative. The method includes providing 4-hydroxymethyl indole having the N-1 nitrogen of protected by a protecting group, and substituting the hydroxyl group of the 4-hydroxymethyl indole with a glycyl unit to produce a neo-tryptophan derivative. The protecting group can include Boc. The method can include adding, after the substitution, an additional protecting group to the nitrogen within the glycyl unit. The additional protecting group can include Fmoc.

Another aspect of the invention features a method of making a polypeptide containing neo-tryptophan. The method includes providing a neo-tryptophan derivative, and linking an amino acid residue to the neo-tryptophan derivative to form the polypeptide containing neo-tryptophan (e.g., L-neo-tryptophan or D-neo-tryptophan). The neo-tryptophan derivative can contains a blocking group attached to a nitrogen atom.

Another aspect of the invention features a method of inducing a neurotensin response in a mammal (e.g., human). The method includes administering an effective dose of a polypeptide containing neo-tryptophan to the mammal. The administration can be extracranial (e.g., intraperitoneal, intravenous, intradermal, subcutaneous, oral, or nasal). The neurotensin response can include antinociception, hypothermia, reduction in appetite, reduction in body weight, reduction in body weight gain, preventing or reducing catalepsy (e.g., haloperidol-induced catalepsy), and/or reducing an effect of a CNS stimulant such as apomorphine, amphetamine, or cocaine. For example, the neurotensin response can include reducing a climbing behavior induced by apomorphine. The neurotensin response can include an antipsychotic effect. For example, the polypeptide can reduce the signs or symptoms of schizophrenia in the mammal. The polypeptide can interact with a neurotensin receptor (e.g., a rat or human neurotensin receptor). The polypeptide can be NT64D, NT64L, NT65L, NT66D, NT66L, NT67L, NT69L, NT69L', NT71, NT72, NT73, NT74, NT75, NT76, or NT77.

Another embodiment of the invention features a method of treating a mammal (e.g., human) having a serotonin recognition molecule. The method includes administering a composition to the mammal such that composition interacts with the serotonin recognition molecule (e.g., a serotonin receptor such as a $5HT_{2A}$ receptor). The composition includes neo-tryptophan, a neo-tryptophan derivative, or a serotonin-like neo-tryptophan derivative. The composition can include a polypeptide.

Another aspect of the invention features a method for screening a polypeptide for in vivo use. The method includes contacting a polypeptide containing neo-tryptophan with a protease, and determining whether or not the polypeptide remains intact.

Another aspect of the invention features the use of a polypeptide containing neo-tryptophan in the manufacture of a medicament for treating a mammal.

In another embodiment, the invention features the use of a compound in the manufacture of a medicament for treating a mammal. The compound contains neo-tryptophan, a neo-tryptophan derivative, or a serotonin-like neo-tryptophan derivative.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The invention provides a novel amino acid, neo-tryptophan, as well as polypeptides containing this novel amino acid such as neurotensin analogs. In addition, the invention provides neo-tryptophan derivatives, serotonin-like neo-tryptophan derivatives, and polypeptides containing such derivatives. The invention also provides methods for making neo-tryptophan, neo-tryptophan derivatives, serotonin-like neo-tryptophan derivatives, and compositions containing these compounds. Further, the invention provides methods for inducing a neurotensin response in a mammal as well as methods for treating a mammal having a serotonin recognition molecule.

The invention provides a novel amino acid, neo-tryptophan. Neo-tryptophan can be used to create novel polypeptides having enhanced biological characteristics. For example, the invention provides neo-tryptophan-containing NT polypeptide analogs that exhibit enhanced biological effects as compared to NT itself. Specifically, such NT polypeptide analogs can induce antinociception, hypothermia, thirst, weight loss, appetite suppression, and weight gain reduction. In addition, these NT polypeptide analogs can prevent or reduce catalepsy, such as haloperidol-induced catalepsy, and can prevent or reduce an effect of a CNS stimulant such as apomorphine, amphetamine, and cocaine.

The incorporation of neo-tryptophan into a polypeptide sequence can create polypeptide analogs that exhibit increased biological activity, increased resistance to degradation by proteases (e.g., metalloendopeptidases 24.11 and 24.16), and increased blood brain barrier permeability. For example, neo-tryptophan can be used to make polypeptide analogs that interact with their receptors at a higher affinity than the natural polypeptide ligands. In addition, neo-tryptophan can be used as a novel fluorescence probe for spectroscopic studies since neo-tryptophan may have a unique fluorescence profile.

Figure 1:
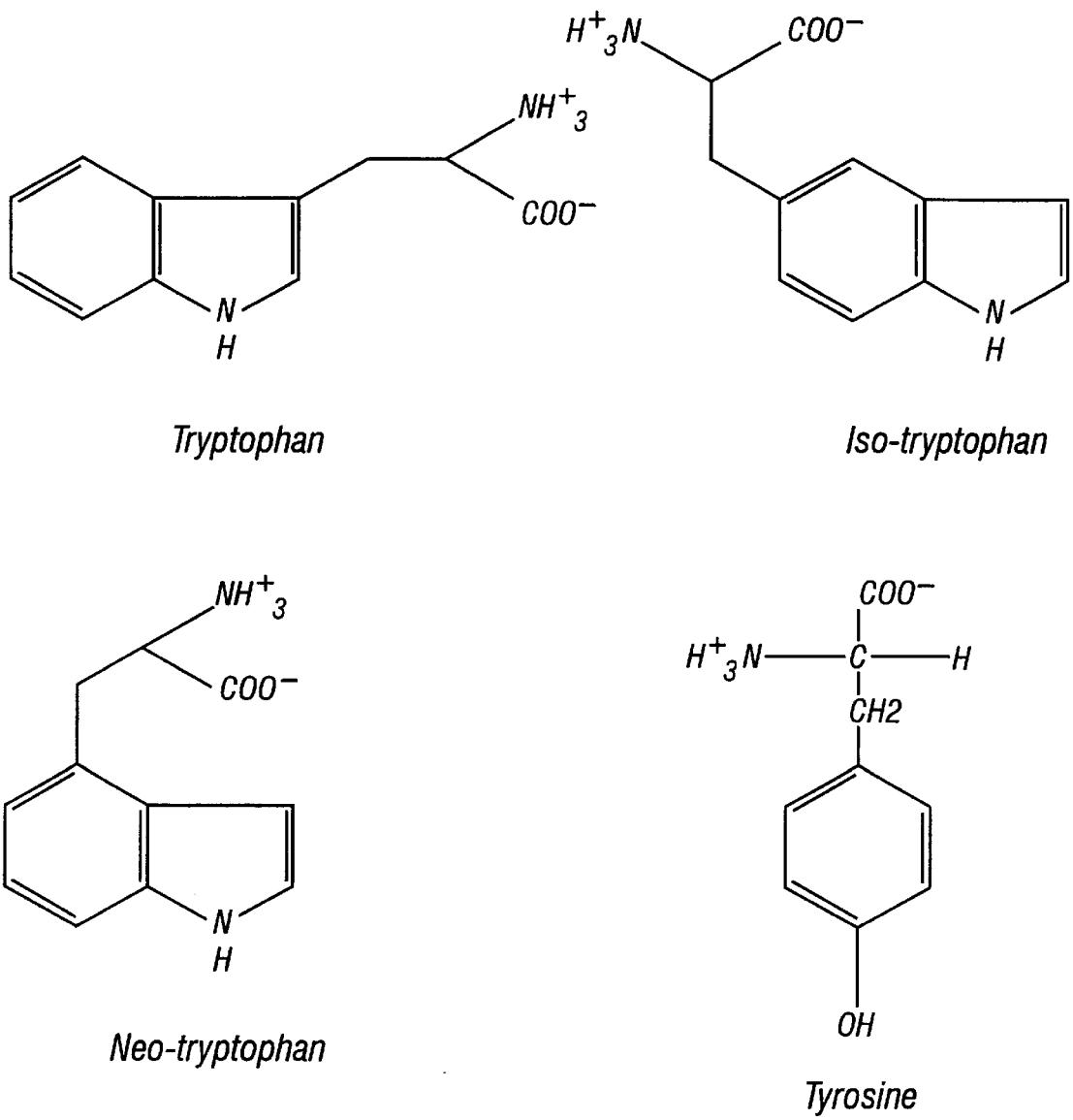
FIG. 1 is a diagram depicting the chemical structure of tryptophan, iso-tryptophan, neo-tryptophan, and tyrosine.

The chemical structures for tryptophan, iso-tryptophan, tyrosine, and neo-tryptophan are provided in FIG. 1. Neo-tryptophan (2-amino-3-[1H-indolyl]propanoic acid) places the indole group of tryptophan in such a unique orientation in terms of steric and electrostatic fields that polypeptides containing neo-tryptophan provide novel arrangements for side chain interactions. It will be appreciated that the term "neo-tryptophan" includes both D-neo-tryptophan and L-neo-tryptophan.

Figure 3:
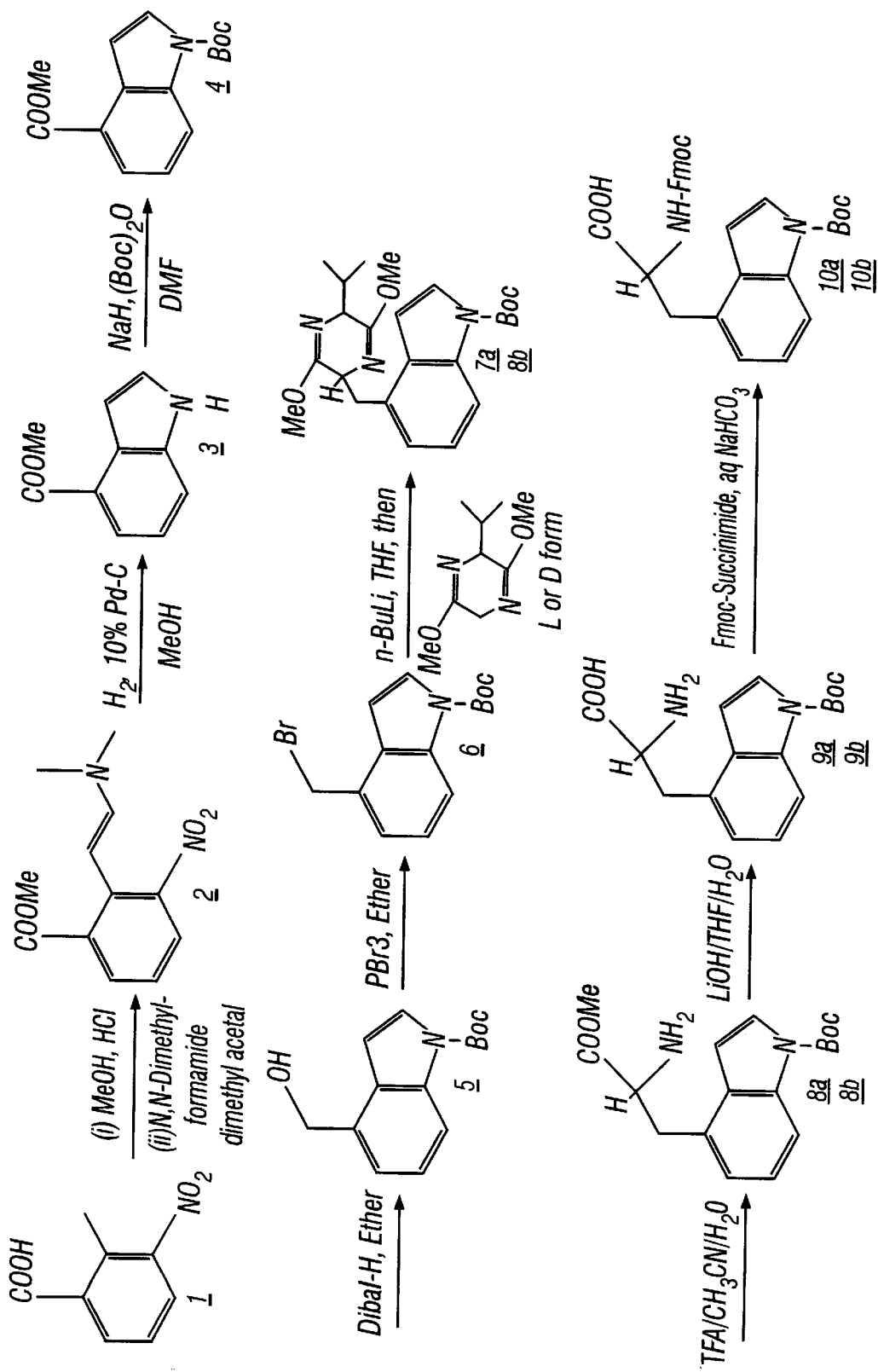
FIG. 3 is a diagram depicting a scheme used to chemically synthesize both D- and L-neo-tryptophan. Series "a" compounds, prepared from (R)-2,5-dihydro-3,6-dimethoxy-2-isopropylpyrazine, and series "b" compounds, prepared from (S)-2,5-dihydro-3,6-dimethoxy-2-isopropylpyrazine, lead to the synthesis of (L)-Fmoc-Boc-protected-neo-tryptophan "10a" and (D)-Fmoc-Boc-protected-neo-tryptophan "10b", respectively.
Figure 4:
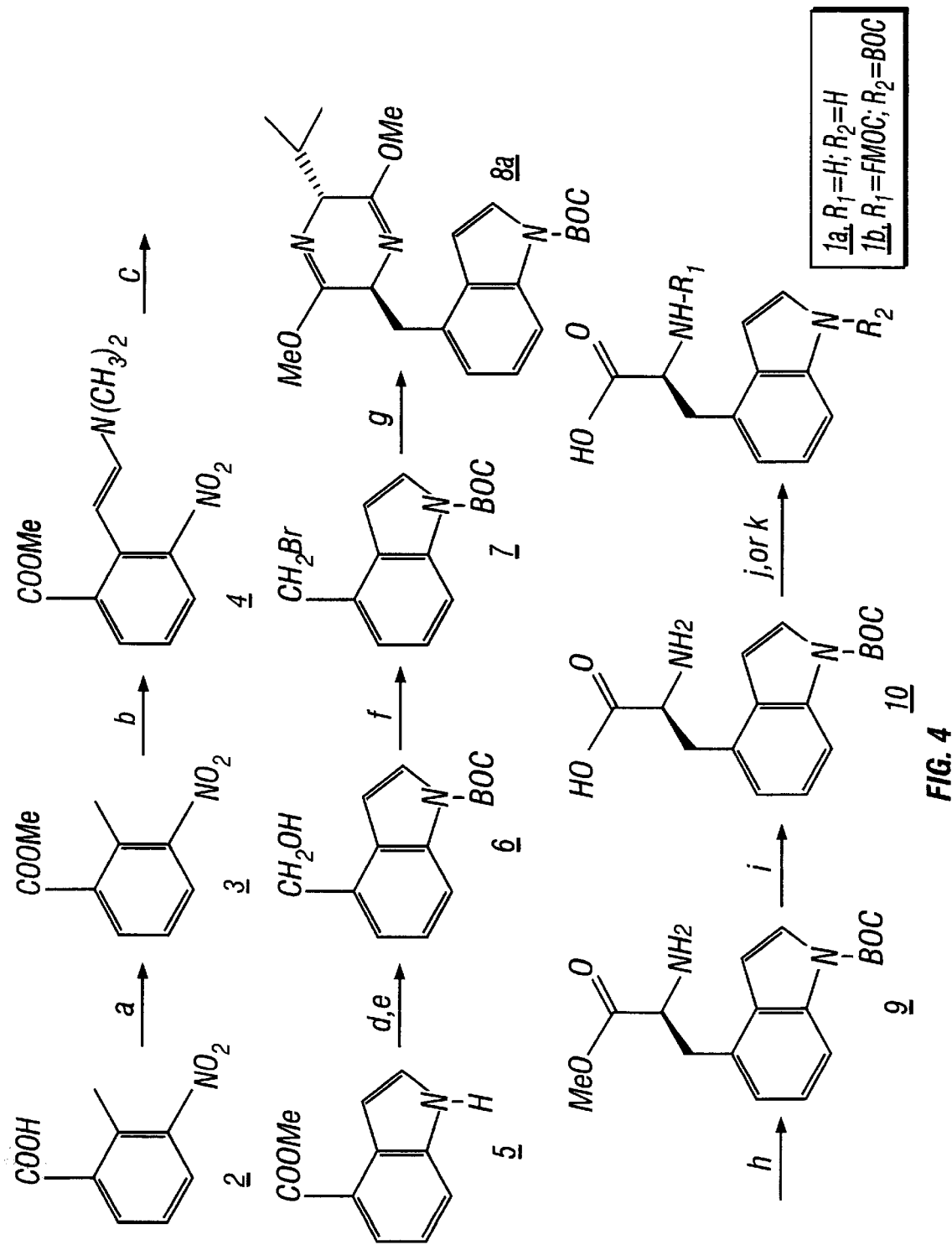
FIG. 4 is a diagram depicting a scheme used to chemically synthesize neo-tryptophan.

The invention provides methods for making neo-tryptophan and neo-tryptophan derivatives. Specifically, any method that results in the production of neo-tryptophan or a neo-tryptophan derivative is within the scope of the invention. For example, one method within the scope of the invention involves substituting the hydroxyl group of 4-hydroxymethyl indole with a glycyl unit such that neo-tryptophan or a neo-tryptophan derivative is produced. In addition, FIGS. 3 and 4 provide methods that can be used to synthesize both D- and L-neo-tryptophan as well as neo-tryptophan derivatives that contain blocking groups. Briefly, these methods involve (a) providing 2-methyl-3-nitrobenzoic acid, (b) esterifying the 2-methyl-3-nitrobenzoic acid to form an esterification product, (c) reacting the esterification product with N,N-dimethylformamide dimethylacetal to produce an enamine product, (d) performing reductive cyclization on the enamine product to produce a 4-substituted indole methyl ester, (e) protecting the indole nitrogen of the 4-substituted indole methyl ester with a Boc group, (f) reducing the protected 4-substituted indole methyl ester with DIBAL to produce N-Boc-4-hydroxymethyl indole, (g) converting the N-Boc-4-hydroxymethyl indole into benzylic bromide, (h) performing $SN_2$ displacement of the bromide of the benzylic bromide with a carbanion to produce diastereomeric bislactim products, (i) isolating one of the diastereomeric bislactim products, (j) hydrolyzing the isolated diastereomeric bislactim product to produce an aminoester product, (k) saponifying the aminoester product to produce an $N^{ind}$-t-Boc amino acid, and (l) removing the Boc group to produce neo-tryptophan. Other methods within the scope of the invention can be easily devised by one skilled in the art once provided with the teachings disclosed herein.

The term "neo-tryptophan derivative" as used herein refers to any compound that has the basic structure of neo-tryptophan. Neo-tryptophan derivatives include, without limitation, neo-tryptophan having an additional chemical group added to the glycyl group or to the indole structure. For example, one or both of the nitrogen atoms can be modified to contain a blocking group such as Fmoc or Boc. One such modification can result in a neo-tryptophan derivative having a Boc blocking group attached to the indole nitrogen atom and a Fmoc blocking group attached to the glycyl group nitrogen atom. Neo-tryptophan derivatives can be used during polypeptide synthesis reactions to produce polypeptides that contain neo-tryptophan.

Any composition containing neo-tryptophan or a neo-tryptophan derivative is within the scope of the invention. Such compositions can include, without limitation, lipids, carbohydrates, amino acids, polypeptides, nucleic acids, peptide nucleic acids, and combinations thereof. Compositions containing neo-tryptophan or a neo-tryptophan derivative can be in an aqueous or non-aqueous form. For example, a neo-tryptophan-containing composition can contain water or saline.

Any polypeptide containing neo-tryptophan or a neo-tryptophan derivative is within the scope of the invention. Such polypeptides can contain any sequence of natural or synthetic amino acids provided at least one residue is neo-tryptophan or a neo-tryptophan derivative. In other words, any amino acid residue within a polypeptide can be replaced with neo-tryptophan or a neo-tryptophan derivative. For example, D- or L-neo-tryptophan can be substituted for D- and L-isomers of the aromatic amino acid residues (i.e., tryptophan, tyrosine, and phenylalanine) in natural and synthetic polypeptides. Again, the incorporation of neo-tryptophan or a neo-tryptophan derivative into an amino acid sequence can improve a polypeptide's binding affinities, selectivity, blood brain barrier permeability, and/or resistance to peptidase degradation. Examples of polypeptides that can be modified to contain neo-tryptophan or a neo-tryptophan derivative include, without limitation, adrenocorticotropic hormone, angiotensin, bombesin, bradykinin, kalledin, calcitonin gene related peptide, BDNF, EGF, somatostatin, enkephalin (e.g., met-enkephalin, leu-enkephalin, and their derivatives), dermorphin, substance P, proctolin, isotocin, vasopressin, vasotocin, luteinizing hormone releasing hormone, neurotensin, thyrotropin releasing hormone, endomorphin-1, endomorphin-2, and morphiceptin.

The invention provides methods for making polypeptides that contain neo-tryptophan and neo-tryptophan derivatives. Specifically, any method that results in the production of a polypeptide that contains neo-tryptophan or a neo-tryptophan derivative is within the scope of the invention. For example, one method within the scope of the invention involves linking an amino acid residue to neo-tryptophan or a neo-tryptophan derivative to form a polypeptide. For the purpose of this invention, the term "polypeptide" includes, without limitation, dipeptides as well as polypeptides larger than dipeptides. In addition, polypeptides containing neo-tryptophan or a neo-tryptophan derivative can be synthesized using common polypeptide synthesis techniques with the substitution of neo-tryptophan or a neo-tryptophan derivative when appropriate (Morbeck DE et al., In: *Methods: A Companion to Methods in Enzymology* 6:191–200, Academic Press Inc., New York (1993)). For example, polypeptides can be synthesized using Fmoc chemistry with t-butyl-protected side chains, either individually on automated polypeptide synthesizers (ABI 430A or 431A) or simultaneously on a multiple polypeptide synthesizer (ACT350, Advanced Chemtech, Louisville, Ky.). Protocols concerning activation coupling times, amino acid dissolution, coupling solvents, and synthesis scale can be followed according to the manufacturer's instructions. Further, polypeptides containing neo-tryptophan or a neo-tryptophan derivative can be purified by, for example, reverse-phase HPLC, and then analyzed for purity by, for example, HPLC and mass spectrometry.

The term "substantially pure" as used herein refers to a molecule (e.g., an amino acid or polypeptide) that has been separated from either the components that accompany that molecule in nature or the reaction products (e.g., by-products) from a chemical synthesis process. Typically, a molecule is substantially pure when it is at least 50%, 60%, 70%, 80%, 90%, 95%, 99%, or 99.9%, by weight, free from other components or reaction products. Purity can be measured by any appropriate method (e.g., column chromatography, mass spectrometry, polyacrylamide gel electrophoresis, or HPLC analysis).

Figure 2:
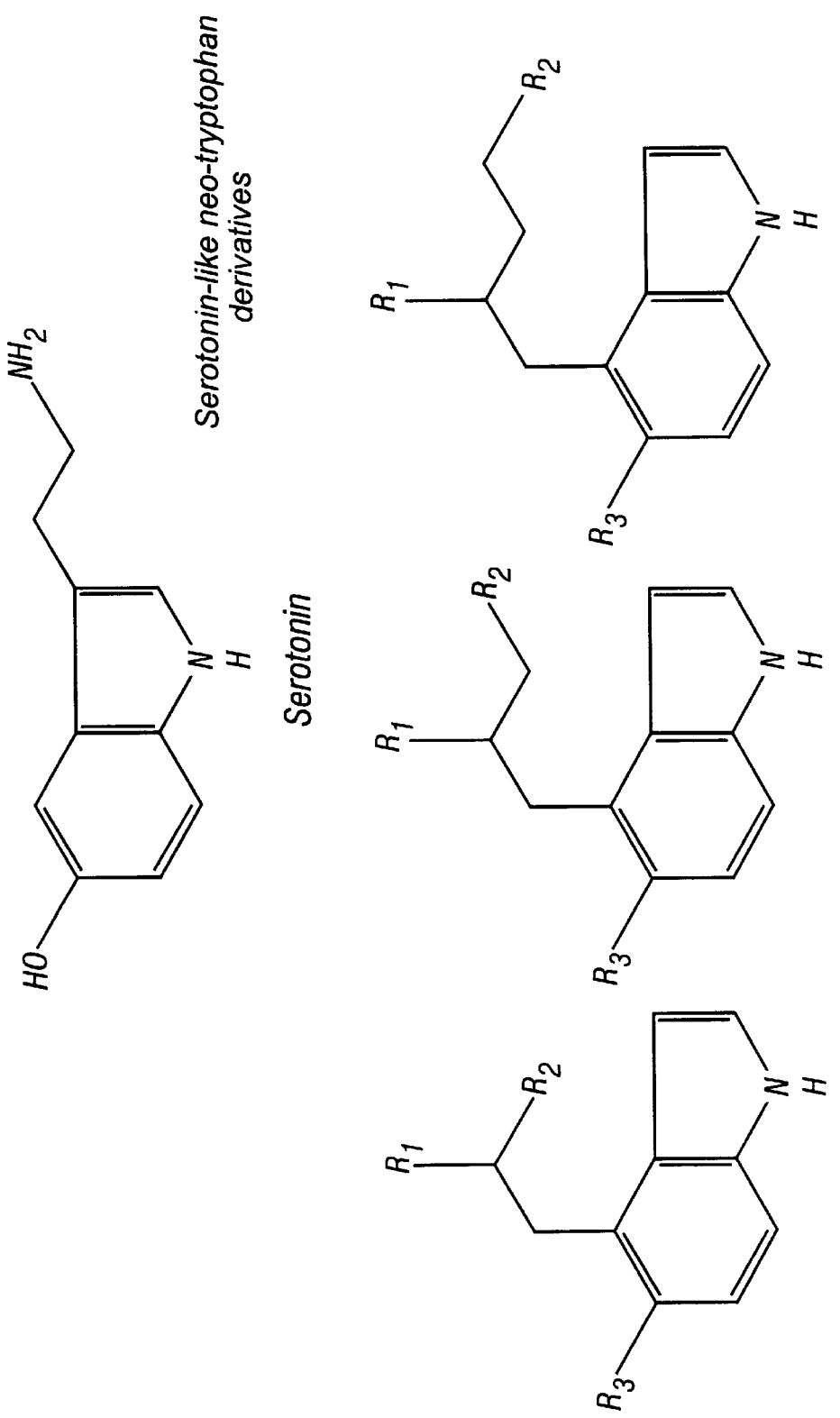
FIG. 2 is a diagram depicting the chemical structure of serotonin and serotonin-like neo-tryptophan derivatives. X can be any chemical group or modification.

The invention also provides serotonin-like neo-tryptophan derivatives (FIG. 2). Such serotonin-like neo-tryptophan derivatives can interact with serotonin recognition molecules such as serotonin receptors and serotonin plasma membrane and vesicular transporters. For example, serotonin-like neo-tryptophan derivatives can be used as serotonin receptor agonists or antagonists, inhibitors of serotonin re-uptake by plasma membrane monoamine transporters, or inhibitors of monoamine packaging into intracellular compartments (e.g., synaptic vesicles) by vesicular monoamine transporters. In other words, the serotonin-like neo-tryptophan derivatives provided by the invention can be used to interact with serotonin recognition molecules in a manner such that serotonergic conditions such as depression, anxiety, migraine, schizophrenia, eating disorders, obsessive compulsive disorders, and panic disorders are influenced.

The chemical structure of serotonin-like neo-tryptophan derivatives is depicted in FIG. 2. In one embodiment, $R_1$ can be a hydroxyl group, $R_2$ can be an amino group, and $R_3$ can be either a hydroxyl group or hydrogen atom. The "X" symbol in FIG. 2 represents any chemical structure or modification including, without limitation, blocking groups such Fmoc and Boc.

Any method can be used to synthesize a serotonin-like neo-tryptophan derivative. For example, neo-tryptophan can be chemically modified using common organic chemistry techniques such that a serotonin-like neo-tryptophan derivative is produced.

In addition, the invention provides methods of inducing a neurotensin response in a mammal (e.g., a rodent, cow, pig, dog, cat, horse, sheep, goat, non-human primate, and human). These methods involve administering an effective dose of a polypeptide containing neo-tryptophan or a neo-tryptophan derivative. A neurotensin response is any biological response that can be attributed to NT or a NT polypeptide analog. For example, a neurotensin response can be a biological response that occurs after a ligand interacts with a receptor (e.g., NTR1 and NTR2) that binds NT. Examples of neurotensin responses include, without limitation, antinociception, hypothermia, antipsychotic effects, loss of appetite, body weight reduction, body weight gain reduction, and increased thirst. Other examples of neurotensin responses include, without limitation, the prevention or reduction of catalepsy, such as haloperidol-induced catalepsy, as well as the prevention or reduction of an effect of a CNS stimulant (e.g., apomorphine, amphetamine, and cocaine). An effect of a CNS stimulant can be, for example, the climbing behavior induced by apomorphine.

The term "effective dose" as used herein refers to any amount of compound that induces the particular described response without inducing significant toxicity. For example, an effective dose of NT69L for appetite reduction can be that amount needed to cause the mammal to exhibit appetite suppression without significant toxicity. In addition, an effective dose of a particular compound administered to a mammal can be adjusted according to the mammal's response and desired outcomes. Significant toxicity can vary for each particular patient and depends on multiple factors including, without limitation, the patient's degree of illness, age, and tolerance to pain.

In addition, any of the materials described herein can be administered to any part of the mammal's body including, without limitation, brain, spinal fluid, blood stream, lungs, nasal cavity, intestines, stomach, muscle tissues, skin, peritoneal cavity, and the like. Thus, a polypeptide containing neo-tryptophan can be administered by intravenous, intraperitoneal, intramuscular, subcutaneous, extracranial, intrathecal, and intradermal injection, by oral administration, by inhalation, or by gradual perfusion over time. For example, an aerosol preparation can be given to a mammal by inhalation. It is noted that the duration of treatment with the materials described herein can be any length of time from as short as one day to as long as a lifetime (e.g., many years). For example, a polypeptide containing neo-tryptophan can be administered at some frequency over a period of ten years. It is also noted that the frequency of treatment can be variable. For example, a polypeptide containing neo-tryptophan can be administered once (or twice, three times, etc.) daily, weekly, monthly, or yearly.

Preparations for administration can include sterile aqueous or non-aqueous solutions, suspensions, and emulsions. Examples of non-aqueous solvents include, without limitation, propylene glycol, polyethylene glycol, vegetable oils, and injectable organic esters. Aqueous carriers include, without limitation, water as well as alcohol, saline, and buffered solutions. Preservatives, flavorings, and other additives such as, for example, antimicrobials, anti-oxidants, chelating agents, inert gases, and the like may also be present.

Any polypeptide containing neo-tryptophan or a neo-tryptophan derivative that induces a neurotensin response can be administered to a mammal. Such polypeptides can be identified by, for example, monitoring any of the biological characteristics described herein before and after administration. In addition, a polypeptide that induces a neurotensin response can interact with a neurotensin receptor (e.g., a rat or human neurotensin receptor). The term "interaction" as used herein means that two components specifically bind each other. Typically, any compound that has a binding affinity for a particular compound in the sub-millimolar range (e.g., $K_d < 1$ mM) is considered to interact with that particular compound. For example, a ligand that binds a receptor with an affinity less than 1 mM specifically interacts with that receptor. Examples of polypeptides that interact with a NT receptor include, without limitation, NT64D, NT64L, NT65L, NT66D, NT66L, NT67L, NT69L, NT69L', NT71, NT72, NT73, NT74, NT75, NT76, and NT77.

The invention also provides methods for treating a mammal having a serotonin recognition molecule. The methods involve administering a composition containing neo-tryptophan, a neo-tryptophan derivative, or a serotonin-like neo-tryptophan derivative such that the composition interacts with a serotonin recognition molecule. The term "serotonin recognition molecule" includes receptors as well as transporters (e.g., plasma membrane and vesicular transporters). The interaction between the composition and serotonin recognition molecule can either stimulate or inhibit serotonergic activity, and thus treat conditions such as depression, anxiety, migraine, schizophrenia, eating disorders, obsessive compulsive disorders, and panic disorders.

The invention provides a method for screening a polypeptide for in vivo use. The method involves contacting a polypeptide with a protease and determining whether or not the polypeptide remains intact. The term "protease" as used herein refers to any polypeptide that cleaves a peptide bond. Any source can be used to obtain proteases. For example, biological samples such as blood and intestinal tissue can be used as a source of protease. In addition, any method can be used to determine whether or not a polypeptide remains intact. For example, polyacrylamide gel electrophoresis and HPLC analysis can be used to determine whether or not a polypeptide remains intact.

The invention will be further described in the following examples, which do not limit the scope of the invention described in the claims.

EXAMPLES

Example 1

Synthesis of neo-tryptophan and neo-tryptophan-containing Polypeptides

D- and L-neo-tryptophan were synthesized according to the schemes depicted in FIGS. 3 and 4. Polypeptides containing neo-tryptophan were synthesized as described elsewhere using the neo-tryptophan amino acids when appropriate (Morbeck DE et al., In: *Methods: A Companion to Methods in Enzymology* 6:191–200, Academic Press Inc., New York (1993)). Briefly, polypeptides were synthesized using Fmoc chemistry with t-butyl-protected side chains, either individually on automated polypeptide synthesizers (ABI 430A or 431A) or simultaneously on a multiple polypeptide synthesizer (ACT350, Advanced Chemtech, Louisville, Ky.). Protocols concerning activation coupling times, amino acid dissolution, coupling solvents, and synthesis scale were followed according to the manufacturer's instructions. All polypeptides were purified by reverse-phase HPLC using a C18 column (2.2× 25 cm; Vydac, Hesperia, Calif.) in 0.1% TFA/water and a gradient of 10%–60% acetonitrile in 0.1% TFA/water. A combination of analytical HPLC and mass spectrometry was used to analyze polypeptide purity.

The following methods were used for the convenient, multigram synthesis of neo-tryptophan. The Fmoc-t-Boc derivative of neo-tryptophan was readily incorporated into bioactive synthetic peptides using standard solid phase synthesis. The synthesis of neo-tryptophan featured the use of Schöllkopf chiral auxiliary reagents for chirality induction during a key step. For convenience, alpha-numerical designations are used to describe specific compounds used in the synthesis steps depicted in FIG. 4. In addition, a description of these compounds and the reaction procedures are provided.

In general terms, as depicted in FIG. 4, the enantiomeric synthesis of neo-tryptophan 1a and neo-tryptophan derivative 1b began with 2-methyl-3-nitrobenzoic acid 2 which, after esterification, was followed by reaction with N,N-dimethylformamide dimethylacetal to furnish the enamine 4. Reductive cyclization using $H_2$/Pd-C gave the 4-substituted indole methyl ester 5. Protection of the indole nitrogen of the 4-substituted indole methyl ester 5 with the tert-butoxycarbonyl (Boc) group and reduction of the resulting ester with DIBAL proceeded uneventfiilly to give N-Boc-4-hydroxymethyl indole 6. It is noted that the indole nitrogen was initially protected with a benzyl or carbobenzyloxy (Cbz) group but these groups turned out to be problematic later in the synthetic sequence. Specifically, the indole nitrogen benzyl group could not be removed with catalytic hydrogenolysis, and the Cbz group gave low yields due to its partial removal during the reduction of the methyl ester moiety with DIBAL. Next, conversion to the benzylic bromide 7 with phosphorus tribromide in ether was followed by the key $SN_2$ displacement of the bromide with the carbanion derived from commercially available (R)-Schöllkopf reagent, (2R)-2-isopropyl-3,6-dimethoxy-2,5-dihydropyrazine, to provide the diastereomeric bislactim products 8a and 8b in 10:1 diastereomeric excess in 67% yield. The desired diastereomer 8a was readily isolated by flash silica gel chromatography and then subjected to mild acid (0.1 M TFA/$CH_3CN$) treatment that only hydrolyzed the bislactim leaving the Boc group unaffected. The resulting aminoester 9 was saponified to produce $N^{ind}$-t-Boc neo-tryptophan 10. It is noted that the TFA-salt of the aminoester 9 was easily isolated in pure form by extraction with methylene chloride leaving the corresponding (D)-valine aminoester in the aqueous phase. Finally, the amino nitrogen was protected with flourenylmethoxycarbonyl (Fmoc) to form Fmoc/Boc neo-tryptophan derivative 1b. The Fmoc/Boc neo-tryptophan derivative 1b was conveniently incorporated into bioactive peptides using commonly employed solid phase synthesis methods. For spectral, chemical, and optical characterization, the t-Boc group of $N^{ind}$-t-Boc neo-tryptophan 10 was removed to furnish neo-tryptophan 1a. Following the above protocol, multigram synthesis of enantiopure Fmoc/Boc neo-tryptophan derivative 1b was achieved. Since the S-enantiomer of the Schöllkopf reagent is commercially available, the (R)-2-amino-3-(1H-indolyl)propanoic acid was similarly synthesized.

The doubly protected neo-tryptophan 1b was readily incorporated into novel biologically active neurotensin analogs by conventional Fmoc-related automated solid phase chemistry. In addition, neo-tryptophan was incorporated into other polypeptides having biological and therapeutic interest including angiotensin, bradykinin, and Leu-enkephalin (Table I).

TABLE I

Amino acid sequences of NT, angiotensin, bradykinin, and leu-enkephalin polypeptides and polypeptide analogs

| Polypeptide | Sequence | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| NT (SEQ ID NO: 1) | p-Glu | L-Leu | L-Tyr | L-Glu | L-Asn | L-Lys | L-Pro | L-Arg | L-Arg | L-Pro | L-Tyr | L-Ile | L-Leu |
| NT(8–13) (SEQ ID NO: 2) | | | | | | | | L-Arg | L-Arg | L-Pro | L-Tyr | L-Ile | L-Leu |
| NT(9–13) (SEQ ID NO: 3) | | | | | | | | | L-Arg | L-Pro | L-Tyr | L-Ile | L-Leu |

TABLE I-continued

Amino acid sequences of NT, angiotensin, bradykinin, and leu-enkephalin polypeptides and polypeptide analogs

| Polypeptide | 1 | 2 | 3 | 4 | 5 | 6 | 7 | 8 | 9 | 10 | 11 | 12 | 13 |
|---|---|---|---|---|---|---|---|---|---|---|---|---|---|
| NTW (SEQ ID NO: 4) | | | | | | | | L-Arg | L-Arg | L-Pro | L-Trp | L-Ile | L-Leu |
| NT (tert-Leu) (SEQ ID NO: 5) | | | | | | | | L-Arg | L-Arg | L-Pro | L-Tyr | tert-Leu | L-Leu |
| Eisai* (SEQ ID NO: 6) | | | | | | | | N-methyl-Arg | L-Lys | L-Pro | L-Trp | tert-Leu | L-Leu |
| NT2 (SEQ ID NO: 7) | | | | | | | | D-Lys | L-Arg | L-Pro | L-Tyr | L-Ile | L-Leu |
| NT24 "27" (SEQ ID NO: 8) | | | | | | | | L-Arg | D-Orn[&] | L-Pro | L-Tyr | L-Ile | L-Leu |
| NT34 (SEQ ID NO: 9) | | | | | | | | L-Arg | L-Arg | L-Pro | L-3,1'-Nal[#] | L-Ile | L-Leu |
| NT64D (SEQ ID NO: 10) | | | | | | | | L-Arg | L-Arg | L-Pro | D-neo-Trp | L-Ile | L-Leu |
| NT64L (SEQ ID NO: 11) | | | | | | | | L-Arg | L-Arg | L-Pro | L-neo-Trp | L-Ile | L-Leu |
| NT65L (SEQ ID NO: 12) | | | | | | | | L-Arg | L-Arg | L-Pro | L-neo-Trp | tert-Leu | L-Leu |
| NT66D (SEQ ID NO: 13) | | | | | | | | D-Lys | L-Arg | L-Pro | D-neo-Trp | tert-Leu | L-Leu |
| NT66L (SEQ ID NO: 14) | | | | | | | | D-Lys | L-Arg | L-Pro | L-neo-Trp | tert-Leu | L-Leu |
| NT67L (SEQ ID NO: 15) | | | | | | | | D-Lys | L-Arg | L-Pro | L-neo-Trp | L-Ile | L-Leu |
| NT69L (SEQ ID NO: 16) | | | | | | | | N-methyl-Arg | L-Lys | L-Pro | L-neo-Trp | tert-Leu | L-Leu |
| NT69L' (SEQ ID NO: 17) | | | | | | | | N-methyl-Arg | L-Arg | L-Pro | L-neo-Trp | tert-Leu | L-Leu |
| NT71 (SEQ ID NO: 18) | | | | | | | | N-methyl-Arg | DAB[$] | L-Pro | L-neo-Trp | tert-Leu | L-Leu |
| NT72 (SEQ ID NO: 19) | | | | | | | | | D-Lys | L-Pro | L-neo-Trp | tert-Leu | L-Leu |
| NT73 (SEQ ID NO: 20) | | | | | | | | | D-Lys | L-Pro | L-neo-Trp | L-Ile | L-Leu |
| NT74 (SEQ ID NO: 21) | | | | | | | | | DAB | L-Pro | L-neo-Trp | tert-Leu | L-Leu |
| NT75 (SEQ ID NO: 22) | | | | | | | | | DAB | L-Pro | L-neo-Trp | L-Ile | L-Leu |
| NT76 (SEQ ID NO: 23) | | | | | | | | L-Arg | D-Orn | L-Pro | L-neo-Trp | L-Ile | L-Leu |
| NT77 (SEQ ID NO: 24) | | | | | | | | L-Arg | D-Orn | L-Pro | L-neo-Trp | tert-Leu | L-Leu |
| Angiotensin (SEQ ID NO: 25) | Asp | Arg | Val | Tyr | Ile | His | Pro | Phe | | | | | |
| Ang1 (SEQ ID NO: 26) | Asp | Arg | Val | L-neo-Trp | Ile | His | Pro | Phe | | | | | |
| Bradykinin (SEQ ID NO: 27) | Arg | Pro | Pro | Gly | Phe | Ser | Pro | Phe | Arg | | | | |
| Brdy1 (SEQ ID NO: 28) | Arg | Pro | Pro | Gly | L-neo-Trp | Ser | Pro | Phe | Arg | | | | |
| Leu-enkephalin (SEQ ID NO: 29) | Tyr | Gly | Gly | Phe | Leu | | | | | | | | |
| Lenk1 (SEQ ID NO: 30) | L-neo-Trp | Gly | Gly | Phe | Leu | | | | | | | | |

*Tsuchiya Y et al., (1989) European Patent Application 89104302.8; [#]naphthalylalanine; [$]diaminobutyric acid; [&]D-ornithine The reagents and conditions used during the steps indicated in FIG. 4 can be summarized as follows: (a) $K_2CO_3$, MeI, DMF, RT (100%); (b) N,N-dimethylformamide dimethylacetal, DMF, 120° C.; (c) $H_2$, 10% Pd-C (cat), MeOH, RT, 50–55 Psi, benzene (67% over 2 steps); (d) $(Boc)_2O$, $CH_3CN$, DMAP (cat), RT (100%); (e) DIBAL-H, $CH_2Cl_2$/ether, −78° C. (88%); (f) $PBr_3$, ether/$CH_2Cl_2$ (95%); (g) (2R)-2-isopropyl-3,6-dimethoxy-2,5-dihydropyrazine/BuLi, THF, −78° C., then 7 (67%); (h) 0.1 M aq. TFA, $CH_3CN$, RT, (100% overall); (i) LiOH, $H_2O$, THF/$H_2O$, RT (62%); (j) TFA/$CH_2Cl_2$, RT; (k) Fmoc-Suc, 10% $NaHCO_3$, acetone, 0° C.-RT, (72%).

The following section provides a detailed description of the chemical steps used to synthesize neo-tryptophan. In addition, the nuclear magnetic spectra ($^1H$, $^{13}C$) described herein were measured with a Bruker WH-300 instrument ($^1H$ frequency 300 MHZ, $^{13}C$ frequency 75 MHZ) in the solvent noted. $^1H$ chemical shifts are expressed in parts per million downfield from $Me_4Si$ used as internal standard. Melting points (mp.) were taken with a GallenKamp instrument and are uncorrected. The column chromatographic separations were performed with 'J. T. Baker' Silica gel (40 μm). Anhydrous DMF was obtained from Aldrich Chemicals. Tetrahydrofuran (THF) and diethyl ether were distilled over sodium benzophenone ketyl before use. Methylene chloride was distilled over calcium hydride or $P_2O_5$. Acetonitrile was reagent grade obtained from E.M. SCIENCE, and was used without further drying. Ethyl acetate and hexane were reagent grade, and used as received. The purity of all compounds was shown to be >95% by TLC as well as by high field $^1$H NMR and $^{13}$C NMR (300 and 75 MHZ Brucker instrument). Optical rotations were taken with a 241-Perkin Elmer Polarimeter (Na lamp). IR spectra were measured with a 2020 GALAXY Series FT-IR (Mattson Instruments).

With reference to FIG. 4, DMF (130 mL) was added to a well mixed 2-methyl-3-nitrobenzoic acid 2 (50 g, 0.28 mol) and $KHCO_3$ (84 g, 0.84 mol) solution. Since the mixture became highly viscous, it was heated to 40° C. with manual shaking. Iodomethane (79 g, 0.56 mol) was added via syringe after the gas evolution had ceased. The resulting orange colored solution was stirred for 12 hours at room temperature. The reaction mixture was poured into water (800 mL), and the resulting precipitate collected by filtration and dried over $P_2O_5$ to give pure methyl 2-methyl-3-nitrobenzoate 3 (56 g, 100%) as a white solid: mp. 64.2–65.5° C.; $^1$H-NMR ($CDCl_3$) δ 8.00 (d, J=7.8 Hz, 1H), 7.85 (d, J=8.0 Hz, 1H), 7.39 (t, J=8.0 Hz, 1H), 3.95 (s, 3H), 2.63 (s, 3H); IR (KBr, $cm^{-1}$) 1724, 1548, 1279; MS (EI): 195 ($M^+$).

A solution of methyl 2-methyl-3-nitrobenzoate 3 (20 g, 0.1 mol) and N,N-dimethylformamide dimethyl acetal (40 mL, 0.3 mol) in DMF (50 mL) was stirred at 120° C. under nitrogen for 12 hours. The solution became deep red. The excess amount of N,N-dimethylformamide dimethyl acetal and DMF was distilled off under reduced pressure to give crude enamine 4 that was directly used in the next step without purification.

The crude enamine 4 was dissolved in anhydrous benzene (250 mL). Pd/C (10%, 2.8 g) was added to this solution, and the resulting mixture was hydrogenated at 55 psi. Warming was observed at the start of the reaction. The deep red mixture became dark gray after 12 hours at room temperature. Pd/C was filtered off over Celite, and the filtrate was concentrated under reduced pressure. Chromatography on silica gel (ethyl acetate/hexanes: 30:70 v/v, Rf=0.55) afforded methyl 1H-4-indolecarboxylate 5 (11.8 g, 67%) as a light yellow solid: mp. 67.5–69.0° C.; $^1$H-NMR ($CDCl_3$) δ 8.40 (s, 1H), 7.93 (d, J=8.3 Hz, 1H), 7.60 (d, J=8.9 Hz, 1H), 7.36 (t, J=3.0 Hz, 1H), 7.26 (t, J=3.7 Hz, 1H), 7.26–7.18 (m, 1H), 4.0 (s, 3H): IR (KBr, $cm^{-1}$) 3322, 1705, 1279; MS (ESI): 176 ($M^+$+1).

Di-tert-butyl dicarbonate (14.7 g, 67.4 mmol) and DMAP (0.2 g) was added to a solution of methyl 1H-4-indolecarboxylate 5 (11.8 g, 67.4 mmol) in acetonitrile (50 mL). The mixture was stirred at room temperature for 12 hours. Some bubbling was observed. Solvent was removed under reduced pressure to give a residue that was redissolved in ethyl acetate (200 mL). The solution was washed sequentially with cold 1N HCl (80 mL), water (50 mL), and brine (50 mL), and then dried ($MgSO_4$). The solvent was removed under reduced pressure to give pure 1-(tert-butyl) 4-methyl 1H-1,4-indoledicarboxylate (18.5 g, 100%) as a light yellow oil: $^1$H-NMR ($CDCl_3$) δ 8.41 (d, J=8.2 Hz 1H), 7.98 (d, J=7.7 Hz, 1H), 7.71 (d, J=3.7 Hz, 1H), 7.36 (t, J=7.9 Hz, 1H), 7.28 (d, J=3.8 Hz, 1H), 3.98 (s, 3H) 1.68 (s, 9H); $^{13}$C-NMR ($CDCl_3$) δ 187.3, 149.4, 135.9, 130.5, 127.8, 125.4, 123.5, 121.9, 119.7, 107.8, 84.1, 51.8, 28.1; IR (KBr, $cm^{-1}$) 1703, 1603, 1283, 1146; MS (ESI): 276 ($M^+$+1).

DIBAL (1.0 M in $CH_2Cl_2$, 163 mmol) was added at −78° C. in 30 minutes under nitrogen to a solution of 1-(tert-butyl) 4-methyl 1H-1,4-indoledicarboxylate (18.5 g, 67 mmol) in ether (150 mL). Stirring was continued at this temperature for another 30 minutes at which point the reaction was quenched with saturated citric acid at −78° C. A precipitate immediately formed that, after warming to room temperature, was acidified to pH 1 with 1N HCl and extracted with ethyl acetate (3×200 mL). The combined extracts were washed sequentially with water (100 mL), and brine (200 mL), and then dried ($MgSO_4$). The solvent was evaporated under vacuum to give a residue that was purified by chomatography on silica gel (ethyl acetate/hexanes: 30/30 v/v, Rf=0.45) yielding tert-butyl 4-(hydroxymethyl) 1H-1-indolecarboxylate 6 (14.5 g, 88%) as a light yellow solid: mp. 62.9–64.1° C. $^1$H-NMR ($CDCl_3$) δ 8.09 (d, J=8.1 Hz 1H), 7.6 (d, J=3.7 Hz, 1H), 7.28 (t, J=7.5 Hz, 1H), 7.20 (d, J=7.3 Hz, 1H), 6.69 (d, J=3.7 Hz, 1H), 4.90 (s, 2H), 2.01 (s, 1H), 1.67 (s, 9H); $^{13}$C-NMR ($CDCl_3$) δ 149.7, 135.3, 132.7, 128.8, 125.9, 124.2, 121.2, 114.8, 105.2, 83.7, 63.4, 28.1; IR (KBr, $cm^{-1}$) 3364, 1732, 1130; MS (ESI): 248 ($M^+$+1).

$PBr_3$ (2.4 mL. 25.8 mmol) was added dropwise at 0° C. under nitrogen to a stirred solution of tert-butyl 4-(hydroxymethyl) 1H-1-indolecarboxylate 6 (6.0 g, 24.3 mmol) in ether (80 mL) and $CH_2Cl_2$ (20 mL) under nitrogen. The reaction was completed 30 minutes after the addition. The mixture was poured into a cold aqueous $NaHCO_3$ solution (100 mL) and extracted with ethyl acetate (3×80 mL). The combined extract was washed sequentially with water (80 mL), and brine (80 mL), then dried ($MgSO_4$), filtered, and finally concentrated to provide tert-butyl 4-(bromomethyl)-1H-1-indolecarboxylate 7 (6.3 g, 84%) as an oil which was immediately taken to the next step.

n-BuLi (2.5 M in hexane) was added dropwise via syringe to a solution of (2R)-2-isopropyl-3,6-dimethoxy-1,5-dihydropyrazine (3.8 g, 20.4 mmol) in THF (70 mL) under nitrogen at −78° C. The carbanion was allowed to form for 10 minutes at the same temperature, at which point a solution of tert-butyl 4-(bromomethyl)-1H-1-indolecarboxylate 7 in THF (40 mL) was added in a dropwise fashion. The reaction proceeded to completion in one hour at −78° C. Saturated aqueous $NH_4Cl$ (80 mL) was added at −78° C., and the THF was evaporated under reduced pressure. The aqueous phase was extracted with ethyl acetate (3×80 mL). The combined extracts were washed with brine (100 mL), dried ($MgSO_4$), and concentrated. The residue was purified on silica gel column (ethyl acetate/hexanes: 5/95 then 10/90 v/v, Rf=0.60 for the major product) to afford tert-butyl 4-{[(2S,5R)-5-isopropyl-3,6-dimethoxy-2,5-dihydro-2-pyrazinyl]methyl}-1H-1-indolecarboxylate 8a (5.8 g, 67%) as a colorless oil: $[α]_D^{25}$=+26.7 (c=14.8 mg/mL, $CHCl_3$); $^1$H-NMR ($CDCl_3$) δ 7.98 (d, J=8.2 Hz 1H), 7.54 (s, 3H), 7.17 (t, J=7.8 Hz, 1H), 6.96 (d, J=7.3 Hz, 1H), 6.69 (d, J=4.0 Hz, 1H), 4.45–4.38 (m, 1H), 3.69 (s, 3H), 3.61 (s, 3H), 3.45–3.20 (m, 3H), 2.15–2.05 (m, 1H), 1.67 (s, 9H), 0.91 (d, J=6.8 Hz, 3H), 0.58 (d, J=6.8 Hz, 3H); $^{13}$C-NMR ($CDCl_3$) δ163.7, 162.2, 149.8, 134.9, 131.0, 130.0, 125.0, 124.0, 121.8, 113.3, 106.5, 83.4, 60.1, 56.7, 52.3, 52.1, 36.9, 31.1, 28.2, 18.9, 16.4; IR (KBr, $cm^{-1}$) 1734, 1696, 1346, 1128; MS (ESI): 414 ($M^+$+1).

TFA (0.15 N, 24 mmol) was added to a solution of tert-butyl 4-{[(2S,5R)-5-isopropyl-3,6-dimethoxy-2,5-dihydro-2-pyrazinyl]methyl}-1H-1-indolecarboxylate 8a (3.5 g, 8.6 mmol) in acetonitrile (95 mL). The mixture was purged with nitrogen and stirred for 12 hours at room temperature. The acetonitrile was evaporated, and the water phase extracted with $CH_2Cl_2$ (5×60 mL). The combined extract was washed sequentially with water (3×100 mL), and brine (80 mL), and then dried ($MgSO_4$). Filtration and evaporation of the solvent left tert-butyl 4-[(2S)-2-amino-3-methoxy-3-oxopropyl]-1H-1-indolecarboxylate 9 (2.7 g, 98%) as a colorless oil: $[\alpha]_D^{25}$=+17.6 (c=12.8 mg/mL, $CHCl_3$); $^1$H-NMR ($CDCl_3$) δ 8.06 (d, J=8.3 Hz 1H), 7.61 (d, J=3.7 Hz, 1H), 7.26 (t, J=7.6 Hz, 1H), 7.06 (d, J=3.7 Hz, 1H), 3.84 (dd, J=5.1, 8.1 Hz, 1H), 3.70 (s, 3H), 3.36 (dd, J=5.1, 13.5 Hz, 1H), 3.06 (dd, J=8.2, 13.6 Hz, 1H), 1.67 (s, 9H), 1.46 (s 2H); $^{13}$C-NMR ($CDCl_3$) δ 175.4, 149.7, 135.2, 130.2, 129.5, 125.8, 124.3, 114.0, 105.3, 83.7,55.5, 52.0, 38.5, 28.1; IR (neat, cm$^{-1}$) 3383, 1732, 1346,1155; MS (ESI): 319 (M$^+$+1).

LiOH.$H_2O$ (980 mg, 26 mmol) dissolved in $H_2O$ (100 mL) at room temperature was added to a solution of tert-butyl 4-[(2S)-2-amino-3-methoxy-3-oxopropyl]-1H-1-indolecarboxylate 9 (2.7 g, 8.5 mmol) in THF (200 mL). The reaction was (close monitoring by TLC) judged complete after 10 minutes. After neutralizing with 1N HCl (30 mL), the THF and most of the water were evaporated in vacuo. The precipitated product $N^{ind}$-t-Boc neo-tryptophan ((2S)-2-amino-3-[1-(tert-butoxycarbonyl)-1H-4-indolyl] propanoic acid) 10 (1.8 g, 62%) was collected by filtration, and dried over $P_2O_5$ under high vacuum: mp. 169.5–171.2° C. (dec). $[\alpha]_D^{25}$=−9.85 (c=6.6 mg/mL, EtOH); $^1$H-NMR (DMSO-d$_6$) δ 7.89 (d, J=8.2 Hz 1H), 7.69 (d, J=3.8 Hz, 1H), 7.27 (t, J=7.7 Hz, 1H), 7.14 (d, J=7.5 Hz, 1H), 6.96 (d, J=3.8 Hz, 1H), 3.99 (t, J=6.6 Hz, 1H), 3.45–3.26 (m, 2H), 1.63 (s, 9H); $^{13}$C-NMR (DMSO-d$_6$) δ 170.3, 149.1, 134.6, 130.0. 128.0, 126.0, 124.3, 123.8, 113.7, 105.8, 83.8, 53.3, 33.5, 27.6; IR (KBr, cm$^{-1}$) 3432, 3179, 1734, 1603, 1051; MS (ESI): 305 (M$^+$+1).

A mixture of $N^{ind}$-t-Boc neo-tryptophan 10 (1.8 g, 5.28 mmol) in 10% aqueous $NaHCO_3$ (30 mL) was stirred for one hour at room temperature. After adding a solution of Fmoc-Suc (1.9 g, 5.55 mmol) in acetone (30 mL) to this mixture, the resulting mixture was stirred for 12 hours at room temperature. Acetone was evaporate under reduced pressure. The aqueous phase was acidified to pH 5 with 1N HCl, and extracted with ethyl acetate (3×60 mL). The combined extracts were washed with brine (80 mL), then dried ($Na_2SO_4$), and concentrated. The resulting residue was purified on silica gel (MeOH/$CH_2Cl_2$: 5/95 v/v. Rf=0.3) as a white solid yielding the Fmoc/Boc derivative of neo-tryptophan ((2S)-3-[1-(tert-butoxycarbonyl)-1H-4-indolyl]-2-{[(9H-fluorenylmethoxy)carbonyl]amino} propanoic acid) 1b: mp. 92.1–93.8° C. $[\alpha]_D^{25}$=+5.5 (c=3.6 mg/mL, $HCCl_3$); $^1$H-NMR (DMSO-d$_6$) δ 7.93 (d, J=8.2 Hz 1H), 7.87 (d, J=7.6 Hz, 2H), 7.78 (d, J=8.7 Hz, 1H), 7.67 (d, J=6.0 Hz, 1H), 7.59 (dd, J=7.5 10.6 Hz, 2H), 7.45–7.36 (m, 2H), 7.36–7.19 (m, 3H), 7.15 (d, J=7.2 Hz, 1H), 6.85 (d, J=3.6 Hz, 1H), 4.34–4.23 (m, 1H), 4.23–4.10 (m, 2H), 3.41–3.32 (m, 2H), 3.20–3.08 (m, 1H), 1.62 (s, 9H); $^{13}$C-NMR (DMSO-d$_6$) δ 173.4, 156.0, 149.2, 143.9, 140.8, 134.6, 130.7, 129.9, 127.8, 127.2 126.0, 125.4, 124.3, 123.6, 120.2, 113.3, 105.8, 84.0, 65.8, 55.2, 46.6, 34.2, 27.8; IR(KBr, cm$^{-1}$) 3308, 1703, 1346, 1128; MS (ESI): 563 (M+K$^+$), 549 (M+Na$^+$).

A solution of $N^{ind}$-t-Boc neo-tryptophan 10 (10 mg, 0.03 mmol) in TFA (1 mL) and $CH_2Cl_2$ (2 mL) was stirred for 90 minutes. Solvent was evaporated under reduced pressure. The residue was purified on reverse phase HPLC on a Vydak C$_8$ column (15–20 μm particle size, 250×22 mm i.d) using a gradient of 10% B to 90% B in 30 minutes (buffer A: 0.1% TFA in $H_2O$; buffer B: 80% $CH_3CN$ in buffer A; UV detection at λ$_{max}$ 220 nm; Flow rate 8 mL/min) to give neo-tryptophan ((2S)-2-amino-3-(1H-4-indolyl)propanoic acid) 1a as a trifluoroacetate salt: mp. 110.0–111.8° C. $[\alpha]_D^{25}$=+31.8 (c=1.1 mg/mL, $H_2O$); $^1$H-NMR (DMSO-d$_6$) δ 11.22 (s, 1H), 8.27 (s, 3H), 7.42–7.34 (m, 2H), 7.04 (t, J=7.6 Hz 1H), 6.87 (d, J=7.1 Hz, 1H), 6.35 (s, 1H) 4.17 (s, 1H), 3.41–3.26 (m, 2H); IR (KBr, cm$^{-1}$) 3399, 1736; MS (ESI): 205 (M$^+$+1).

Example 2

Neurotensin Receptor Binding Properties of neo-tryptophan-containing Polypeptides CHO-K1 cells were stably transfected with nucleic acid encoding either the human NTR1 or the rat NTR1, and cultured in 150 mm petri plates with 35 mL of Dulbecco-modified Eagle's medium containing 100 μM minimal essential medium nonessential amino acids (GIBCO) supplemented with 5% (v/v) FetalClone II bovine serum product (Hyclone Labs, Logan, Utah). CHO cells (subculture 9–19) were harvested at confluency. Briefly, the medium from each plate was removed by aspiration, and the cells washed with 6 mL of 50 mM Tris-HCl (pH 7.4) and resuspended in 5–10 mL of Tris-HCl by scraping the cells with a rubber spatula. The resuspended cells were placed into a centrifuge tube and collected by centrifugation at 300×g for five minutes at 4° C. in a GPR centrifuge (Beckman Instruments, Fullerton, Calif.). The cellular pellet (in 50 mM Tris-HCl, 1 mM EDTA, pH 7.4) was stored at −180° C. until radioligand binding was performed.

For binding assays, crude membranal preparations were prepared by centrifugation of the cellular pellet at 35,600×g for ten minutes. The supernatant was decanted and discarded, and the cellular pellet was resuspended in 2 mL of Tris-HCl, 1 mM EDTA (pH 7.4) followed by homogenization with a Brinkmann Polytron at setting 6 for ten seconds. Centrifugation was repeated as above and the supernatant was decanted and discarded. The resulting final cellular pellet was resuspended in 50 mM Tris-HCl, 1 mM EDTA, 0.1% bovine serum albumin, and 0.2 mM bacitracin. Polypeptide concentration of the membranal preparation was estimated by the method of Lowry et al. (*J. Biol. Chem.* 193:265–275 (1951)) using bovine serum albumin as a standard.

A Biomek 1000 robotic workstation was used for all pipetting steps in the radioligand assays as previously described (Cusack and Richelson, *J. Recept. Res.* 13:123–34 (1993)). Competition binding assays with [$^3$H]NT (1 nM), varying concentrations of unlabeled NT, and polypeptide analogs were carried out with membranal preparations from the appropriate cell lines. Nonspecific binding was determined with 1 μM unlabeled NT in assay tubes with a total volume of 1 mL. Incubation was at 20° C. for 30 minutes. Each reaction was terminated by addition of cold 0.9% NaCl (5×1.5 mL) followed by rapid filtration through a GF/B filter strip that had been pretreated with 0.2% polyethylenimine. Details of binding assays are described elsewhere (Cusack et al., *Mol. Pharmacol.* 44:1036–1040 (1993)). The data were analyzed using the LIGAND program (Munson and Rodbard, *Anal. Biochem.* 107:220–239 (1980)). The values presented for $K_d$ are expressed as the geometric means ±SEM (Fleming et al., *J. Pharmacol. Exp. Ther.* 182:339–345 (1972) and DeLean et al., Mol. Pharmacol. 21:5–16 (1982)).

Radioligand binding assays were performed using various NT analogs. In each case, the equilibrium dissociation constant ($K_d$) was derived for both human NTR1 and rat NTR$_1$ (Table II). All polypeptides tested had a Hill Coefficient close to unity, indicating that binding was to a single class of receptors. Substituting L-neo-tryptophan for Tyr$^{11}$ in NT (8-13) resulted in the most potent compound (NT64L) tested at the human receptor, and nearly the most potent tested at the rat receptor. In fact, the binding affinity of NT64L was in the range of that found for [L-3, 1'-Nal$^{11}$] NT(8-13) (NT34) at the rat receptor. NT72, a pentapeptide, was found to be the least potent at both receptors. While substituting D-Lys for L-Arg$^8$ in NT64L resulted in a polypeptide (NT67L) exhibiting greater resistance to peptidase degradation than NT64L, the NT67L polypeptide exhibited a binding affinity ($K_d$=0.61 nM) about six fold lower at the human receptor than that exhibited by NT64L ($K_d$=0.09 nM). In addition, steric factors appear to influence NT receptor binding since the results revealed a more than 30 fold reduction in binding affinity for NT64D, which contains the D-isomer of neo-tryptophan, and for NTW, which contains the natural isomer of tryptophan, when compared to NT64L.

TABLE II

Comparison of binding affinity for NT analogs at human and rat NT receptors.

| Polypeptide | $K_d$[nM] hNTR | $K_d$[nM] rNTR |
|---|---|---|
| NT64L | 0.09 ± 0.01 (3) | 0.10 ± 0.01 (5) |
| NT(8–13) | 0.14 ± 0.01 (4) | 0.16 ± 0.01 (3) |
| NT65L | 0.32 ± 0.01 (5) | 0.075 ± 0.004 (3) |
| NT67L | 0.61 ± 0.06 (3) | 0.21 ± .02 (10) |
| NT2 | 1.0 ± 0.1 (6) | 0.8 ± 0.1 (3) |
| NT69L | 1.55 ± 0.09 (5) | 0.82 ± 0.07 (4) |
| NT71 | 1.8 ± 0.1 (4) | 0.22 ± 0.03 (8) |
| NT(1–13) | 1.97 ± 0.07 (130) | 2.39 ± 0.08 (99) |
| NTW | 3.2 ± 0.3 (3) | 0.34 ± 0.03 (3) |
| NT64D | 3.3 ± 0.4 (3) | 3.8 ± 0.4 (3) |
| NT66L | 3.7 ± 0.4 (3) | 0.85 ± 0.09 (14) |
| NT34 | 5.8 ± 0.6 (4) | 0.046 ± 0.003 (3) |
| NT(tert-Leu) | 13.2 ± 0.5 (4) | 19.8 ± 0.4 (4) |
| NT(9–13) | 30 ± 2 (3) | 46 ± 4 (3) |
| NT75 | 34 ± 1 (5) | 10.0 ± 0.4 (5) |
| NT73 | 45 ± 3 (3) | 32 ± 6 (6) |
| Eisai | 95 ± 9 (12) | 5.4 ± 0.6 (8) |
| NT66D | 210 ± 20 (10) | 77 ± 9 (8) |
| NT74 | 360 ± 10 (3) | 160 ± 40 (3) |
| NT72 | 640 (2) | 270 ± 30 (5) |

Values are geometric mean ± SEM, n value is in parenthesis; $K_d$ = equilibrium dissociation constant in CHO-K1 membranes; n.d. = no data.

In general, substitution of L-Ile$^{12}$ with tert-Leu, a substitute for the natural amino acid leucine, lowered the binding affinity of the NT analogs when compared to their counterparts containing L-Ile$^{12}$. For example, NT(tert-Leu) was about 100 fold less potent at both the human ($K_d$=13.2 nM) and rat ($K_d$=19.8 nM) receptors than was NT(8-13) ($K_d$= 0.14 nM and 0.16 nM at human and rat receptors, respectively). A smaller decrease (3 fold) in binding affinity resulted when L-Ile$^{12}$ was replaced with tert-Leu as observed between NT64L and NT65L.

The Eisai compound was found to be almost 20 fold weaker at the human NT receptor when compared to its binding affinity at the rat receptor. Substituting L-Trp$^{11}$ in Eisai with L-neo-tryptophan to give NT69L resulted in a 60 fold increase in binding affinity at the human receptor, but only a 6 fold increase at the rat receptor.

Other modifications included substitutions in the sequence of NT(9-13). Briefly, NT(9-13) was found to have low affinity for NT receptors. In fact, NT(9-13) was over 200 fold weaker at the human and rat receptors than was NT(8-13). Of the pentapeptides tested (NT72, NT73, NT74, and NT75), NT75 was found to be the most potent ($K_d$=34 nM and 10 nM at the hNTR1 and rNTR1, respectively). These pentapeptides, however, were not more potent than NT(9-13). Again, substitution of Ile$^{12}$ with tert-Leu caused a several fold reduction in binding affinity as observed when NT75 is compared to NT74, and when NT73 is compared to NT72.

Figure 5:
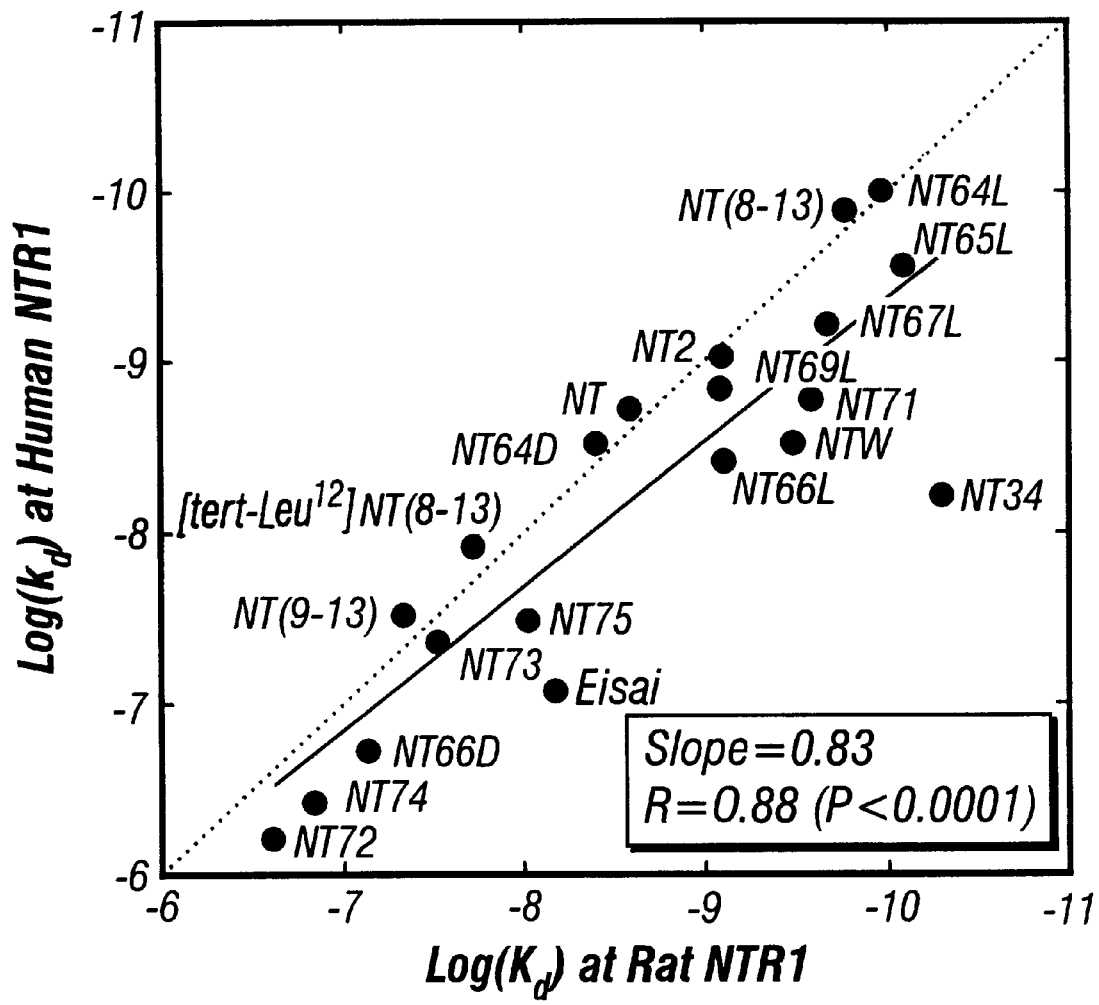
FIG. 5 is a graph plotting the $K_d$ values obtained using the human NT receptor for the indicated NT polypeptide analogs against the respective $K_d$ values obtained using the rat NT receptor.

The $K_d$ values obtained using the human NT receptor for the various NT analogs were plotted against the respective $K_d$ values obtained using the rat receptor (FIG. 5). This analysis revealed a strong correlation (R=0.88, P<0.0001) between the binding affinity at human and rat NT receptors. In addition, the line of identity (dotted line having slope=1) revealed that most NT analogs have a higher binding affinity for the rat receptor than for the human receptor, while some have a similar binding affinity for both receptors. No NT analog exhibited a higher binding affinity for human NTR1 than for rat NTR1.

In summary, every tested NT analog containing L-neo-tryptophan exhibited an increase in binding affinity over similar NT analogs (e.g., NTW vs. NT64L, NT2 vs. NT67L, and Eisai vs. NT69L). Thus, the addition of L-neo-tryptophan contributed significantly to increasing the potency of NT analogs.

Example 3

PI Turnover Properties of neo-tryptophan-containing Polypeptides

To measure PI turnover, intact CHO-K1 cells were harvested at about 80% confluency. Cells were detached from the petri plates by removal of culture medium followed by incubation of the cellular monolayer for 20 minutes at 37° C. with gentle shaking in a modified Puck's D$_1$ solution containing 2 mM EGTA. The details of assaying the relative changes in PI turnover in intact cells using a radioactively labeled precursor was described elsewhere (Pfenning and Richelson, In: *Methods in Neurotransmitter Receptor Analysis* Eds: Yamamura HI, SJ Enna and MJ Kuhar, pp. 147–175, Raven Press, New York (1990)). Briefly, intact CHO cells were prelabeled with D-myo-[$^3$H]inositol (18.3 Ci/mmol) in the presence of lithium chloride (final concentration, 10 mM). Cells were then stimulated with NT or the appropriate NT analog, and the amount of [$^3$H]inositol 1-phosphate ([$^3$H]IP$_1$) produced by the cells isolated chromatographically on Dowex 1-X8 (200–400 mesh). For the experiments described herein, the stimulation time was 30 minutes, and the number of CHO cells per assay tube was 1.5×10$^5$. The presented EC$_{50}$ values are expressed as the geometric means ±SEM (Fleming et al., *J. Pharmacol. Exp. Ther.* 182:339–345 (1972) and DeLean et al., Mol. Pharmacol. 21:5–16 (1982)).

Each tested NT analog was finctionally coupled to PI turnover as determined using intact CHO-K1 cells (Table III). The most potent NT analog tested at the human NTR1 was NT67L (EC$_{50}$=0.83 nM). Substituting Ile$^{12}$ in NT67L with tert-Leu to give NT66L did not improve potency at the human NTR1 (EC$_{50}$=10 nM). For NT69L, an EC$_{50}$ of 2.3 nM and 1.3 nM at the hNTR1 and rNTR1, respectively, was observed.

TABLE III

Comparison of PI turnover results for NT analogs at human and rat NT receptors.

| | PI Turnover EC$_{50}$ [nM] | |
|---|---|---|
| Polypeptide | hNTR | rNTR |
| NT64L | 2.8 ± 0.5 (4) | 2.3 ± 0.2 (3) |
| NT(8–13) | 1.5 ± 0.1 (3) | n.d. |
| NT67L | 0.83 ± 0.09 (3) | 13 ± 2 (3) |
| NT69L | 2.3 ± 0.5 (3) | 1.34 ± 0.02 (3) |
| NT(1–13) | 5.0 ± 0.3 (39) | 6.8 ± 0.4 (10) |
| NTW | 110 ± 20 (5) | n.d. |
| NT66L | 10 ± 2 (4) | 1.9 ± 0.4 (3) |
| NT34 | 130 ± 20 (3) | 2.8 ± 0.2 (4) |
| NT(9–13) | 380 ± 50 (3) | n.d. |
| Eisai | 300 ± 20 (4) | 3.1 ± 0.4 (3) |

Values are geometric mean ± SEM, n value is in parenthesis; EC$_{50}$ = concentration of compound needed to stimulate 50% of maximum PI response in intact CHO-K1 cells; n.d. = no data.

In general, the EC$_{50}$ values observed for the various tested analogs were similar at rat NTR1 (in the 1–13 nM range). At the human NT receptor, however, the EC$_{50}$ values were quite different (in the 1–300 nM range for the hexapeptides tested). These results may reflect the size of the binding site at the human NTR1 and the conformation of the NT analog-receptor complex, with the human receptor being much less tolerant of size and steric changes of the ligand. In addition, the Eisai analog was nearly 100 fold weaker at the human NT receptor than at the rat NT receptor (EC$_{50}$ of 300 nM at human NTR1, and 3.1 nM at rat NTR1). This difference was less striking than that found for the respective affinities in radioligand binding experiments with membranal preparations from these cells (Table II). In addition, comparing results obtained using the Eisai analog to those obtained using NT69L revealed an improvement for NT69L in the potency at PI turnover of about 130 fold at human NTR1 and about two fold at rat NTR1. Thus, these results indicate that the addition of L-neo-Trp to NT analogs significantly influences their pharmacology and biochemistry at human NTR1.

Example 4

Degradation Properties of neo-tryptophan-containing Polypeptides

The following experiments determined the stability of the novel polypeptides containing neo-tryptophan in rat and human plasma as well as rat intestinal preparations. Whole blood was collected into tubes containing heparin (200 units/mL), and placed on ice. Samples were spun at 500×g for ten minutes. The supernatant was recovered and frozen at –20° C. overnight. The samples were thawed at room temperature and spun at 500×g for ten minutes. After recovery, the supernatant was filtered through 0.2 μm syringe filter.

For degradation studies, ultrapure water that had been filtered twice through 0.02 μm filters was used. Each polypeptide to be tested was resuspended in this water at a concentration of 1 mg/mL. The filtered plasma was diluted 1:1 with the filtered H$_2$O (50% v/v). Then, 500 μL of diluted plasma was combined with 500 μL of the polypeptide solution (1 mg/nL), and vortexed. The final concentration of polypeptide was 0.5 mg/nl in 25% plasma (v/v).

An initial time point was taken at 0° C. before placing the plasma/polypeptide sample in a 37° C. water bath. At each time point, 50 μL of the plasma/polypeptide sample was removed and combined with 1.050 mL of filtered H$_2$O, representing a 1:22 dilution. Thus, the final amount of material injected into the HPLC represents 22.7 μg of polypeptide in 1.14% plasma. Peak area was recorded at each time point and compared to the plasma/polypeptide sample at zero time at 0° C. Values are expressed as the percent of peak area at zero time.

The HPLC conditions were as follows: C-18 column; flow rate equal to 3 mL/minute; and the gradient equal to 10–90% B in 50 minutes, where A=TFA, 0.1% and B=TFA 0.1% in 80% acetonitrile.

For intestinal preparations, rats were sacrificed by decapitation, and the small intestines removed. The tissue was washed with ice-cold PBS (10 mM, pH 7.4). About 2 mg of intestinal tissue was added to about 10 mL of PBS and homogenized using a Brinkman polytron homogenizer (setting 6). After homogenization, 10 mL of PBS was added to 10 mL of the intestinal homogenate. The mixture was then centrifuged at 500×g for 15 minutes at 4° C. The supernatant was removed and stored at –20° C. until testing. Immediately before incubation with the polypeptide, the intestinal preparation was filtered through a 0.2 μm filter. Testing procedures were similar to those for the plasma tests.

For the degradation studies, data were plotted in linear form as a semi-log plot with SigmaPlot for Windows Version 4.00. Linear regression on these plots provided the parameters used to calculate the half-time ($t_{1/2}$) for degradation of each polypeptide. The correlation coefficient (R) for the linear regression was taken as a measure of the goodness-of-fit.

L-neo-tryptophan provided increased resistance to peptidases. The half-life of NT2 in human plasma was determined to be about 0.85 hours (Table IV). Substituting L-Tyr[11] of NT2 with L-neo-tryptophan resulted in a polypeptide (NT67L) having a half-life in human plasma of about 96 hours. In addition, substituting L-Trp[11] of Eisai with L-neo-tryptophan resulted in a polypeptide (NT69L) having a longer half-life in human plasma. These results demonstrate that the substitution of amino acid residues with neo-tryptophan can produce polypeptides having increases resistance to degradation.

TABLE IV

Half-life values for Neurotensin (NT) and NT analogs.

| | Plasma | | | | Rat Intestinal Preparation | |
|---|---|---|---|---|---|---|
| | Human | | Rat | | | |
| Polypeptide | half-time (hours) | R | half-time (hours) | R | half-time (hours) | R |
| NT | 1.9 | 0.99 | 5.4 | 1.0 | 0.04 | 1.00 |
| NT(8–13) | n.d. | | 0.22 | 0.98 | n.d. | |
| NT2 | 0.85 | 0.71 | n.d. | | n.d. | |
| NT64L | 1.4 | 0.96 | n.d. | | n.d. | |
| NT65L | 1.1 | 1.00 | n.d. | | n.d. | |
| NT66L | 170 | 0.94 | 350 | 0.94 | n.d. | |
| NT67L | 96 | 0.97 | 130 | 0.95 | 0.77 | 0.94 |
| NT69L | 500 | 0.90 | 250 | 0.88 | 4.1 | 0.91 |
| NT71 | n.d. | | 260 | 0.72 | 5.1 | 0.98 |
| NT72 | 3000 | 0.19 | n.d. | | 54 | 0.99 |
| NT73 | 300 | 0.58 | n.d. | | 0.83 | 0.99 |
| NT74 | n.d. | | 110 | 1.00 | n.d. | |
| NT75 | n.d. | | 1.6 | 0.93 | 0.27 | 0.96 |
| Eisai | 460 | 0.91 | n.d. | | 22 | 0.96 |

These degradation studies also revealed some difference between human and rat plasma. For example, NT had a half-life in human plasma of about one-third that observed in rat plasma. In general, however, the half-life times observed for the tested analogs correlated reasonably well between the human and rat plasma samples (slope=0.76, R=0.97, df=3, P=0.03). In human plasma, NT, NT2, NT64L, and NT65L were the most rapidly degraded. The remaining analogs tested all had significantly longer half-life times in human plasma. In addition, all hexapeptide NT analogs containing a substitution for Arg$^8$ and all pentapeptide NT analogs containing a substitution for Arg$^9$ were found to be substantially resistant to degradation. Similar results were obtained using the rat plasma.

NT72 was found to be the most resistant to degradation by rat intestinal proteases, while NT67L, an analog relatively stable in plasma, was degraded very rapidly by rat intestinal proteases. Interestingly, NT69L was less stable in the rat intestinal preparation than was the Eisai analog. Again, NT69L was found to be more resistant to human plasma proteases than the Eisai analog. Substituting Ile$^{12}$ of NT73 with tert-Leu resulted in a polypeptide analog (NT72) exhibiting a substantial increase of stability in the intestinal preparation when compared to NT73.

In general, these results demonstrate that NT analogs having unnatural amino acid substitutions at positions 8 and 12 for the hexapeptides and positions 9 and 12 for the pentapeptides are more resistant to degradation in plasma and in the rat intestinal preparation than NT analogs not having such substitutions.

Example 5

Antinociceptive and Hypothermic Properties of neo-tryptophan-containing Polypeptides Male Sprague Dawley rats (Harlan, Prattville, Ala.; 150–250 g) were house in a temperature controlled room with a 12 hour light/dark cycle, and given water and standard rat chow. Testing occurred during the light cycle. Hot plate measurements were performed to assess antinociception, while body temperature measurements were taken to assess hypothermia.

The baseline hot plate measurements and body temperatures were determined immediately prior to each experiment. Briefly, the hot plate was performed to determine pain sensitivity. Thirty minutes after administration of the test compound, the rat was placed on the hot plate and latency was measured. Hot plate measurements were taken on a metal surface (15×20 cm) maintained at a temperature of 52.0±0.15° C. (Al-Rodhan et al., *Brain Res.* 557: 227–235 (1991), and Jensen and Yaksh, *Brain Research* 372:301–312 (1986)). The latency between the time the rat was placed on the surface and the time it licked either of its hind paws was measured. Failure to respond in 30 seconds resulted in ending of the trial and assignment of that latency. Animals were removed immediately after responding or at the cutoff latency. Hot plate tests were scored as the percent of maximum possible effect (% MPE) and calculated using the following equation: % MPE=[(post-drug latency–pre-drug latency)/(cut-off–pre-drug latency)]×100; where the cut-off was 30 seconds. Immediately after completion of the hot plate test, body temperature measurements were taken using a digital thermistor probe inserted into the rectum about 2–4 cm.

For these behavioral and physiological measurements, data were tested for significance with a student's t-test and p<0.05 was considered significant. Preference for the t-test instead of the ANOVA was given due to the reasons cited elsewhere (O'Brien PC, *Biometrics* 39:787 (1983)).

For intraperitoneal (ip) delivery, the test compound was injected into the intraperitoneal cavity while control rats received an equal volume of saline (0.9% NaCl). For nasal delivery, the test compound was dissolved in 4 μL of sterile saline, and the rats lightly anaesthetized with $CO_2$. The rats then were held in a vertical position while 2 μL of the test compound were delivered to each nostril using a polyethylene gel loading tip attached to a Gilson P20 pipettor. The rats remained in a vertical position until it was clear that all the liquid had been inhaled into the nostril. After inhalation, the rats were allowed to recover from the anesthesia which usually occurred within one minute. For subcutaneous (sc) delivery, the test compound was injected into the fold of skin at the back of the neck. Injection volumes were about 100 μL. For oral deliver, a gavage device attached to a syringe that extended into their stomachs was used to ensure complete delivery of the test compound. The volume delivered was about 0.3 mL.

The following methods were used to deliver the test compounds directly into brain. Under sterile conditions, the rats were stereotaxically implanted with stainless steel guide cannulae (26 gauge) into the periaqueductal gray (PAG) region of the rat brainstem under sodium pentobarbital anesthesia (50 mg/kg, ip) as described in detail elsewhere (Jensen and Yaksh, *Brain Res.* 372:301–312 (1986), and Al-Rodhan, *Brain Res.* 557:227–235 (1991)). The coordinates used for PAG cannulations are −5.6 mm posterior from bregma, 1.0 mm lateral from bregma, and 5.5 mm down from the dura. The guide cannula was pre-measured to be 5.5 mm (Plastics One, Roanoke, Va.) and the internal cannula was ordered to fit below the pedestal with a 2.0 mm projection. The guide cannula was then fixed to the skull using a stainless steel screw (⅛ inch) and cranioplastic cement. A stainless steel stilette was then placed in each guide to keep it patent and free of debris. Immediately after surgery, the animals were allowed to recover before returning them to an individual housing cage. All injections began 5–7 days after surgery. If any problem, such as an infection, was observed with an animal after cannulation, then the animal was euthanized immediately by decapitation.

Intraperitoneal administration of NT64L (1 mg/kg) did not induce antinociception as measured by the hot plate test or hypothermia. When injected into the PAG, however, NT64L (18 nmol) induced both antinociception and hypothermia. Specifically, rats receiving NT64L exhibited a peak % MPE value of 76% at 30 minutes, and a peak body temperature reduction of 2.1° C. at 30 minutes. NT and NT24 "27" also did not induce antinociception or hypothermia upon intraperitoneal administration. After PAG administration, rats receiving NT (18 nmol) exhibited a peak % MPE value of 80% at 30 minutes, and a peak body temperature reduction of 1.8° C. at 30 minutes, while rats receiving NT24 "27" (18 nmol) exhibited a peak % MPE value of 20%, and a peak body temperature reduction of 1.1° C. at 30 minutes.

Intraperitoneal administration of NT66D, NT66L, NT67L, NT69L, NT71, NT72, NT73, and Eisai did induce antinociception and hypothermia (Table V).

TABLE V

Antinociception and hypothermia after intraperitoneal administration of NT analogs.

| | 1 mg/kg | | 5 mg/kg | | | |
|---|---|---|---|---|---|---|
| Polypeptide | Peak BT change | Peak % MPE | Peak BT change | Peak % MPE | $ED_{50}$ BT | ED50 % MPE |
| Eisai | −2.9 @ 60 min | 80% @ 90 min | n.d. | n.d. | 0.26 mg/kg @30 min 0.12 mg/kg @90 min | 0.42 mg/kg @ 30 min 0.08 mg/kg @ 90 min |
| NT66D* | −1.0 @ 30 min | 58% @ 30 min | n.d. | n.d. | n.d. | n.d. |
| NT66L | −3.0 @ 240 min | 100% @ 120 min | −5.0 @ 120 min | 100% @ 330 min | 0.45 mg/kg @30 min 0.18 mg/kg @ 60 min | 0.04 mg/kg @ 30 min 0.02 mg/kg @ 60 min |
| NT67L | −1.8 @ 120 min | 70% @ 90 min | n.d. | n.d. | n.d. | n.d. |
| NT69L | −5.3 @ 300 min | 100% @ 300 min | n.d. | n.d. | 0.4 mg/kg @ 90 min | 0.3 mg/kg @ 90 min |
| NT71 | −2.0 @ 40 min | 70% @ 60 min | −2.4 @ 90 min | 79% @ 180 min | n.d. | n.d. |
| NT72 | n.d. | n.d. | −2.8 @ 180 min | 100% @ 120 min | n.d. | n.d. |
| NT73 | n.d. | n.d. | −0.9 @ 90 min | 40% @ 120 min | n.d. | n.d. |

*NT66D was administered at a dose of 0.5 mg/kg instead of 1 mg/kg.

NT69L had potent and long lasting behavioral effects. Specifically, NT69L given intraperitoneally to rats at a dose of 1 mg/kg induced a significant reduction in body temperature, reaching a peak of −5.3° C. This peak reduction of body temperature was reached about 90 minutes after administration and remained significant up to 300 minutes after treatment. In addition, NT69L produced significant and long lasting antinociception. Specifically, a peak % MPE value of 100% was observed for up to about 200 minutes after treatment. Analysis of the time course for NT69L-induced antinociception and hypothermia revealed that the peak antinociception effect (100% MPE) remained for almost three hours after administration while the hypothermia effect began to recover from the peak value of −5° C. at about 90 minutes. One possible explanation for these time course differences is the existence of different NT receptor subtypes that subserve these two different behavioral responses.

The results from a dose response analysis using NT69L indicated that the $ED_{50}$ value for body temperature lowering (hypothermia) was 0.4 mg/kg at 90 minutes, while the $ED_{50}$ value for % MPE (antinociception) was 0.3 mg/kg at 90 minutes. For NT66L, the $ED_{50}$ value was found to be 0.45 mg/kg at 30 minutes for hypothermia, and 0.04 mg/kg at 30 minutes for antinociception. For Eisai, the $ED_{50}$ value was found to be 0.26 mg/kg at 30 minutes for hypothermia, and 0.42 mg/kg at 30 minutes for antinociception. Although the $ED_{50}$ values for Eisai and the neo-tryptophan-containing NT analogs (NT66L and NT69L) may appear similar in degree, their effects were found to be very different. For hypothermia, animals treated with the Eisai compound exhibited a peak reduction in body temperature of about 3° C. at about one hour. NT69L induced a 5.3° C. reduction in body temperature that was maintained for up to five hours. For antinociception, animals treated with the Eisai compound reached peak of about 80% MPE at 90 minutes. This peak level, however, started to drop shortly thereafter, returning to baseline levels at about six hours after administration. The antinociception induced by NT69L, however, was maintained at a significant level for up to five hours.

The effectiveness of NT analogs administered by several routes also was analyzed. For NT69L, the antinociception and hypothermia results observed after subcutaneous administration were similar to those obtained after intraperitoneal administration with the exception that the observed effects after subcutaneous administration appeared to lag behind the effects observed after intraperitoneal administration. Nasal administration of NT69L also produced antinociception and hypothermia. Specifically, NT69L given nasally to rats at a dose of 5 mg/kg induced a reduction in body temperature, reaching a peak of −1.4° C. at 30 minutes, and induced antinociception with a peak % MPE value of 70% at 60 minutes. Thus, the nasal administration of NT69L appeared to induce antinociception more effectively than hypothermia. In addition, oral administration of NT69L (20 mg/kg) induced a reduction in body temperature, reaching a peak of −0.63° C. at 60 minutes, and induced antinociception with a peak % MPE value of 11% at 30 minutes. While the hypothermia response was significant after oral administration of NT69L, the antinociceptive effect was not. Oral administration of NT66L, however, induced significant antinociception and hypothermia. Specifically, oral administration of NT66L (20 mg/kg) induced a reduction in body temperature, reaching a peak of −1.4° C. at 30 minutes, and induced antinociception with a peak %MPE value of 40% at 60 minutes.

Example 6

Interactions Between Brain Receptors and neo-tryptophan-containing Polypeptide In a radiolabeled competitive binding assay, NT64L, NT66L, and NT67L were found to compete with labeled ketanserin for binding at the $5HT_{2A}$ receptor in human brain tissue (Table VI). Specifically, NT64L had a $K_d$ of 6.6 μM at this receptor in a competition binding assay using [$^3$H] ketanserin as the radioligand. In addition, NT2, NT(8-13), and NT(9-13) were found to compete with labeled ketanserin for binding at the $5HT_{2A}$ receptor in human brain tissue. L-neo-tryptophan itself, however, did not compete with labeled ketanserin for binding at the $5HT_{2A}$ receptor. These results indicate that NT analogs can interact with serotonin recognition molecules.

TABLE VI

Binding affinities for serotonin receptors.

| Compound | Kd [nM]<br>Human Brain Tissue<br>$5HT_{2A}$ |
|---|---|
| NT69L | 34600 |
| NT66L | 8700 |
| NT67L | 7400 |
| NT(9–13) | 6340 |
| NT2 | 6800 |
| L-neo-Trp | >100000 |
| NT64L | 6600 |
| NT(8–13) | 4400 |
| Serotonin | 680 |
| Haloperidol | 61 |
| Clozapine | 9.1 |

Additional radiolabeled competitive binding assays were designed to assess the interaction of NT analogs and other ligands with other various types of receptors such as adrenergic and dopamine receptors (Table VII). These studies revealed that NT67L can interact with adrenergic α1 receptors having a $K_d$ value of 6.9 μM. In addition, these studies revealed that L-neo-tryptophan itself does not bind to human NT receptors from CHO cells.

TABLE VII

Comparison of binding at different receptors.

| | $K_d$ (nM) | | | | | |
|---|---|---|---|---|---|---|
| | Human brain tissue | | | | CHO cells | |
| Compound | adrenergic | | Muscarinic | Dopamine | rNTR | hNTR |
| | α1 | α2 | | | | |
| NT66L | 38000 | n.d. | n.d. | 56000 | 0.85 | 3.7 |
| NT67L | 6900 | >100000 | >100000 | >100000 | 0.21 | 0.61 |
| NT69L | n.d. | 58600 | n.d. | 13300 | 0.82 | 1.55 |
| L-neo-Trp | n.d. | n.d. | n.d. | n.d. | n.d. | >100000 |
| Serotonin | n.d. | n.d. | n.d. | n.d. | >100000 | >100000 |
| Haloperidol | 17 | 600 | >10000 | 2.6 | >100000 | >100000 |
| Clozapine | 19 | 16 | 8.5 | 211 | >100000 | >100000 |

Example 7

Neo-tryptophan-containing Polypeptides and CNS Stimulants

Apomorphine was used to assess the ability of NT analogs to act as neuroleptics. Briefly, male Sprague-Dawley rats were pretreated intraperitoneally with either NT69L or saline only. Thirty minutes following pretreatment, the rats received a subcutaneous injection of apomorphine (600 μg/kg). Occasionally, the effectiveness of NT69L was assessed by measuring antinociception and hypothermia just prior to apomorphine administration. Control animals included rats receiving NT69L followed by saline only, and rats receiving no treatment. The apomorphine was dissolved in oxygen-free boiled 0.9% NaCl solution containing 0.1% ascorbic acid and 0.1% metabisulfite to prevent oxidation. The volume of injection was 1 mL/kg under the loose skin at the back of the animal's neck. Immediately following injection, the rats were placed in cages for observation. About 5–10 minutes later, behavioral monitoring was initiated and lasted for one hour. Climbing episodes were measured by observing the number of times the rat moved up and down in a vertical position during a two minute observation period. Statistical analysis was done using the Student's t-test with P<0.05 being considered significant. Graphs and $ED_{50}$ data were generated using GraphPad Prism® software (version 2.01, GraphPad Software, Inc., San Diego, Calif.).

Rats receiving saline followed by apomorphine exhibited distinctive climbing, sniffing, and licking behaviors that lasted for about 60 minutes after treatment. Pretreatment with NT69L (1 mg/kg) 30 minutes before the apomorphine injection caused a long-lasting blockade of the climbing behavior. This NT69L pretreatment, however, did not influence the sniffing and licking behaviors induced by apomorphine. Control animals receiving no treatment or NT69L without apomorphine did no exhibit any of these behaviors. The $ED_{50}$ as determined by non-linear regression analysis for NT69L at 75 minutes after injection of NT69L (45 minutes after injection of apomorphine) was 16 μg/kg (95% confidence interval; 6.1 to 44 μg/kg; R=0.94). At no dose did NT69L affect the oro-facial stereotypies. Thus, NT69L was found to be an extremely potent compound capable of preventing the climbing behavior induced by apomorphine. These results indicate that NT69L may have clinical effects similar to those of an atypical neuroleptic. The site of the blockade of apomorphine-induced climbing by NT69L does not appear to be dopamine, serotonin, or adrenergic receptors since NT69L was found to have a weak affinity for dopamine $D_2$ receptors as well as $5HT_{2A}$ and $α_2$-adrenergic receptors (Table VII).

At 5 mg/kg (ip), a dose of NT69L that completely blocked the effects of the apomorphine-induced climbing behavior, NT69L caused a large reduction in body temperature. Specifically, a change in body temperature of about −3° C. was observed 30 minutes after injection, while a change of about −4° C. was observed at 77 minutes after injection. At 90 minutes, the $ED_{50}$ for NT69L-induced body temperature lowering was 390 μg/kg (95% confidence interval; 110 to 1400 μg/kg, R=0.98). Injection of apomorphine alone caused a more modest reduction of body temperature than did NT69L. The hypothermic effects observed in animals receiving NT69L alone were not different from those observed in animals receiving the combination of NT69L and apomorphine. Thus, the effects of apomorphine and NT69L on body temperature were not additive. The fact that there was no additive effects of these compounds on hypothermia indicates a common site of action or a "ceiling" effect on body temperature lowering. In other words, NT69L may cause the maximum body temperature lowering possible in the animals.

The following experiments were performed to assess the ability of NT69L to cause and influence catalepsy. Male Sprague-Dawley rats (150–250 g) or CD-1 mice (24–26 g) were housed in a temperature-controlled room in groups of five with free access to food and water. The animals were kept on a 12 hour light/dark cycle, and all tests were performed during the light cycle. The test for catalepsy is well established and quite simple (Munkvad et al., *Brain Behav. Evol.* 1:89–100(1968)). Animals received one of three compounds intraperitoneally: NT69L, a typical neuroleptic (haloperidol), or an atypical neuroleptic (clozapine). Thirty minutes after injection, the animals were tested for catalepsy. For rats, the test involved simply placing the animal's fore paws on a suspended metal bar 10 mm in diameter, 11 cm above the counter. The time elapsed until the animal's fore paws touch the counter was recorded. If the rat did not drop to the counter top by four minutes, the rat was removed from the bar. For mice, catalepsy was scored based on the time that the mice maintained a fixed rearing posture against the side of the cage (Adams et al., *Proc. Natl. Acad. Sci. USA* 94:12157–12161 (1997)). The cut-off time was 20 seconds, and each animal was tested three times for each time point.

NT69L at a dose that induced significant hypothermia (5 mg/kg; ip) had no effect on catalepsy scores in rats. At the same dose, NT69L caused no catalepsy in mice. As expected, however, haloperidol caused profound catalepsy at a dose (1 mg/kg) that had minimal effect on body temperature. In addition, the haloperidol administration did not influence the body temperature lowering effect of NT69L when both drugs were given to the same animal. The haloperidol-induced catalepsy was observed at 30 minutes and lasted for at least six hours. The $ED_{50}$ value for haloperidol-induced catalepsy was found to be 130 µg/kg (95% confidence interval: 280 to 520 µg/kg, R=0.998) at 30 minutes; 260 µg/kg (95% confidence interval: 130 to 530 µg/kg, R=1.00) at 60 minutes, and 310 µg/kg (95% confidence interval: 42 to 2300 µg/kg, R=1.00) at 180 minutes.

When animals were injected with NT69L (5 mg/kg; ip) 30 minutes before injecting haloperidol (1 mg/kg; ip), the rats did not exhibit significant cataleptic behavior. When animals were injected with NT69L (5 mg/kg; ip) 30 minutes after injecting haloperidol (1 mg/kg; ip), the moderate catalepsy observed 30 minutes after the haloperidol treatment was reversed by 30 minutes after NT69L treatment. From the 30 minute time point after NT69L treatment, the rats no longer exhibited catalepsy, and remained non-cataleptic for up to four hours from the time of haloperidol injection. These results indicate that NT69L given before haloperidol blocks haloperidol-induced catalepsy, while NT69L given after haloperidol reverses the catalepsy induced by haloperidol.

To determine the $ED_{50}$ value of NT69L for the reversal of the cataleptic effects induced by haloperidol, animals were given haloperidol (120 µg/kg; ip) followed by varying doses of NT69L (ip) 40 minutes later. Catalepsy was scored at 130 minutes. The $ED_{50}$ value for NT69L at reversing the effects of haloperidol was found to be 260 µg/kg (95% confidence interval: 180 to 370 µg/kg, R=1.00). This $ED_{50}$ value was not statistically different (two-tailed t-test, t=0.67, df=6, P=0.53) from the $ED_{50}$ value (390 µg/kg) determined for NT69L-induced hypothermia at 90 minutes. The $ED_{50}$ value for the blockade by NT69L of the apomorphine-induced climbing behavior was significantly lower than the $ED_{50}$ values both for reversing haloperidol-induced catalepsy (t=2.74, df=15, P=0.0152) and hypothermia (t=3.88, df=17, P=0.0012).

Clozapine (a classical, atypical neuroleptic) was also tested for its ability to affect catalepsy caused by haloperidol. At a dosage of 20 mg/kg (ip), clozapine did not cause catalepsy. When haloperidol (1 mg/kg; ip) was injected 30 minutes before clozapine (20 mg/kg; ip), the animals exhibited cataleptic effects similar to those observed in animals receiving haloperidol alone. Pretreatment with clozapine followed by haloperidol, however, modulated the cataleptic effects of haloperidol. This modulation was not statistically significant. In addition, the change in body temperature for the animals receiving treatment with clozapine and/or haloperidol was in the range of −1° C. to −2° C. This temperature reduction range is markedly less than that observed in animal treated with NT69L alone.

These results indicate that NT69L, but not clozapine, completely prevents catalepsy when given before haloperidol. These results also indicate that NT69L, but not clozapine, reverses haloperidol's cataleptic effects when given after haloperidol. Thus, NT69L may have neuroleptic properties in humans and may be useful in the treatment of extrapyramidal side effects caused by neuroleptics such as the irreversible tardive dyskinesia.

Example 8

Chronic Treatment with a neo-tryptophan-containing Polypeptide

The effect of chronic injection of NT69L was tested. Rats were injected with NT69L (1 mg/kg; ip) daily, and tested for antinociception and hypothermia. Antinociception was measured using the hot plate test described herein. Rats exhibited 100% MPE and about 4 degrees body temperature lowering after the first injection. After the second injection on day 2, however, no analgesic effect was observed and the body temperature was lowered only 1.5 degrees. After the third injection on day 3, there was still no analgesic effect and no body temperature lowering was detected. In addition, the rats exhibited catalepsy when injected with haloperidol after the third and fourth days of NT69L injection.

To check if the rats had developed tolerance to NT69L, the rats were challenged with five times (5×) the dose of NT69L (5 mg/kg; ip) after four days of NT69L treatment at 1 mg/kg (ip). The rats exhibited a reduction in body temperature comparable to the reduction normally observed in naive rats injected with NT69L (1 mg/kg; ip) for the first time. The haloperidol-induced cataleptic effect, however, was not reversed upon administration of the 5× dose of NT69L to the chronically treated rats (four day treatment with 1 mg/kg NT69L; ip). In addition, no analgesic effect was observed in the chronically treated rats after challenge with the 5× dose of NT69L.

The effect of chronic treatment with NT69L on the number of NT binding sites within brain was assessed. Rats were treated daily with NT69L (1 mg/kg; ip) for four days. On day five, the rats were treated with 5 mg/kg (ip) NT69L, tested behaviorally, and then sacrificed. The PAG and rest of brain were dissected from the animal and used in NT binding analysis. Briefly, homogenates were prepared from freshly obtained PAG and the rest of brain of rats according to Goedert et al. (*Brain Res.* 304, 71–81 (1984)) with the following modifications: the assay buffer contained the peptidase inhibitors 1,10 phenanthroline (1 µM) and aprotonin (5 mg/ml). For PAG and rest of brain binding assays, tissues were incubated with 0.3 nM [$^{125}$I]NT (NEN, Boston, Mass.) at room temperature for 30 minutes. Total and nonspecific binding was measured and the binding sites were normalized to polypeptide concentrations by BCA protein determination (Pierce Chemical Co., Rockford, Ill.).

Brain tissues from control rats exhibited more [$^{125}$I]NT binding than brain tissues from rats chronically treated with NT69L. Specifically, the PAG tissue from control rats contained 2.34 dpm/µg protein (n=2), while the same tissue from NT69L-treated rats contained 1.89 dpm/µg protein (n=5). Likewise, the rest of brain tissue from control rats contained 3.1 dpm/µg protein (n=2), while the same tissue from NT69L-treated rats contained 2.1 dpm/µg protein (n=5). These results represent about a 20 to 30 percent reduction in [$^{125}$I]NT binding for brain tissue from NT69L-treated animals.

Example 9

Weight Loss Properties of neo-tryptophan-containing Polypeptides

Two groups of male Sprague-Dawley rats (small and large) and one group of genetically obese Zucker rats were used to study the influence of NT69L on various aspects of body weight. The group of small Sprague-Dawley rats weighed about 270 g at the beginning of the study, while the group of large Sprague-Dawley rats weighted about 400 g. Under normal conditions, the small rats exhibit steady growth, and the large rats do not. All animals were individually housed in a room with a 12 hour light/dark cycle. The rats had free access to commercial hard rat chow pellets and tap water. During the study, the rats received 100 µL of either saline only or 1 µg/kg, 10 µg/kg, or 1 mg/kg of NT69L on days 1, 2, 7, 8, 11, and 12. Food intake (g), water consumption (mL), and body weight (g) were recorded daily for 15 days. The results were presented as mean ±SEM, or as % of original weight. The data were compared by variance analysis (unpaired or paired Student's t test) and Rank sum test.

NT69L caused a significant (P<0.001) reduction in body weight gain when injected (ip) into small Sprague-Dawley rats at a dose of 1 µg/kg and 10 µg/kg. The reduction in body weight gain was greatest one day after injection of NT69L. In addition, small rats failed to make-up for the reduction in body weight gain even after the NT69L administration was discontinued. Specifically, small rats receiving saline only exhibited a 29% increase in body weight by the end of 15 days, while small rats receiving 1 µg/kg NT69L exhibited only an 9.0% increase from their original body weight at day 15. Small rats receiving 10 µg/kg NT69L exhibited an 8.4% increase from their original body weight at day 15. Food intake for the small rats was significantly (P<0.003) less than the food intake observed for saline treated control animals throughout the experiment, indicating that the observed reduction in body weight gain after injection of NT69L is attributable in part to less food intake.

The large Sprague-Dawley rats injected (ip) with 1 mg/kg, but not with 1 µg/kg or 10 µg/kg, exhibited a significant reduction in body weight (P<0.003). Specifically, the large rats receiving 1 mg/kg NT69L exhibited a 3.0% reduction in their original body weight, while saline treated control animals exhibited a 2.4% increase in their original body weight by day 15. In addition, food intake for the large rats was significantly (P<0.003) less than the food intake observed for saline treated control animals during the one to two days post NT69L injection. These results indicate that the observed reduction in body weight in NT69L-treated animals is attributable in part to less food intake.

The genetically obese Zucker rats injected (ip) with NT69L (1 mg/kg) also exhibited a significant reduction in weight gain (P<0.009). Specifically, NT69L-treated animals exhibited a 25% increase in their original body weight, while saline-treated control animals exhibited a 31% increase in their original body weight by day 15. Again, food intake by NT69L-treated animals was significantly reduced (P<0.01) during the one to two days post NT69L injection as compared to the food intake of saline-treated control animals.

These results demonstrate the potent effect of NT69L on (1) body weight gain reduction, (2) body weight loss, and (3) appetite when injected (ip) for two consecutive days at four to five day intervals.

The effect of NT69L on blood hormone levels was assessed. Briefly, Sprague-Dawley rats were injected (ip) with either saline (n=20) or 1 mg/kg NT69L (n=20). Five NT69L-treated rats and five control rats were sacrificed by decapitation at one, four, eight, and twenty-four hours post-injection. Brains were harvested and dissected on ice. The different brain sections were kept on dry ice for HPLC analysis. In addition, blood was collected in cold centrifuge tubes with heparin and kept on ice. After collection, the blood was centrifuged at 2500 rpm for ten minutes, and the plasma was collected and stored at −20° C. until analysis. Glucose, thyroxine (T4), thyroid stimulating hormone (TSH), and corticosterone levels were determined by enzyme assay or RIA.

Rats treated with NT69L (1 mg/kg; ip) exhibited a significant increase in blood glucose (P<0.005) and corticosterone (P<0.001) levels as compared to the level observed in saline-treated controls. Specifically, NT69L-treated animals had a glucose level of 221 mg/dL and a corticosterone level of 24.6 µg/dL, while saline-treated animals had a glucose level of 130 mg/dL and a corticosterone level of 6.1 µg/dL at one hour post injection. In addition, rats treated with NT69L (1 mg/kg; ip) exhibited a significant reduction in TSH (P<0.001) and T4 (P<0.02) levels as compared to the level observed in saline-treated controls. Specifically, NT69L-treated animals had a TSH level of 0.9 mIU/L and a T4 level of 1.8 µg/dL, while saline-treated animals had a TSH level of 7.65 mIU/L and a T4 level of 2.6 µg/dL at one hour post injection. By 24 hours post-injection, the levels of blood glucose, corticosterone, TSH, and T4 had returned to the levels observed in control animals, indicating that the hyperglycemia as well as the inhibitory effect of thyroid function due to NT69L were only transitory. The Zucker rats exhibited a similar increase in blood glucose (310 mg/dL for the NT69L-treated vs. 140 mg/dL for the control) and corticosterone (19.7 µg/dL for the NT69L-treated vs. 10.9 µg/dL for the control) levels, and a reduction in TSH (0.43 mIU/L for the NT69L-treated vs. 1.9 mIU/L for the control) and T4 (1.03 µg/dL for the NT69L-treated vs. 1.47 µg/dL for the control) levels one hour after injection (ip) of NT69L (1 mg/kg).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A polypeptide, wherein said polypeptide comprises neo-tryptophan.

2. The polypeptide of claim 1, wherein said polypeptide is substantially pure.

3. The polypeptide of claim 1, wherein said neo-tryptophan is L-neo-tryptophan.

4. The polypeptide of claim 1, wherein said neo-tryptophan is D-neo-tryptophan.

5. The polypeptide of claim 1, wherein said polypeptide interacts with a neurotensin receptor.

6. The polypeptide of claim 1, wherein said polypeptide is a neurotensin analog with neo-tryptophan being located at amino acid position 11 of neurotensin.

7. The polypeptide of claim 1, wherein said polypeptide is selected from the group consisting of NT64D, NT64L, NT65L, NT66D, NT66L, NT67L, NT69L, NT69L', NT71, NT72, NT73, NT74, NT75, NT76, NT77, Ang1, Brdy1, and Lenk1.

8. An amino acid, wherein said amino acid is neo-tryptophan.

9. The amino acid of claim 8, wherein said amino acid is substantially pure.

10. The amino acid of claim 8, wherein said amino acid is L-neo-tryptophan.

11. The amino acid of claim 8, wherein said amino acid is D-neo-tryptophan.

12. A composition, said composition comprising a compound having the following structure:

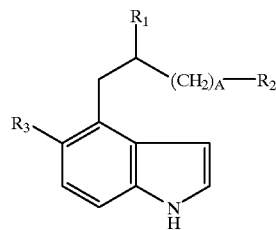

wherein $R_1$, $R_2$, and $R_3$ independently are H, OH, $CH_3$, SH, F, $NH_2$, or COOH, and A is two or three.

13. A composition, said composition comprising a compound having the following structure:

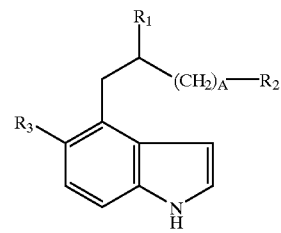

wherein $R_1$ is a hydroxyl group, $R_2$ is an amino group, $R_3$ is a hydroxyl group, and A is zero.

14. A method of synthesizing neo-tryptophan, said method comprising:
   a) providing 4-hydroxymethyl indole, wherein the N-1 nitrogen of said 4-hydroxymethyl indole is protected by a protecting group, wherein said protecting group comprises Boc,
   b) substituting the hydroxyl group of said 4-hydroxymethyl indole with a glycyl unit, and
   c) removing said protecting group after said substitution to produce neo-tryptophan.

15. A method of synthesizing neo-tryptophan, said method comprising:
   a) providing 2-methyl-3-nitrobenzoic acid,
   b) esterifying said 2-methyl-3-nitrobenzoic acid to form an esterification product,
   c) reacting said esterification product with N,N-dimethylformamide dimethylacetal to produce an enamine product,
   d) performing reductive cyclization on said enamine product to produce a 4-substituted indole methyl ester,
   e) protecting the indole nitrogen of said 4-substituted indole methyl ester with a Boc group,
   f) reducing said protected 4-substituted indole methyl ester with DIBAL to produce N-Boc-4-hydroxymethyl indole,
   g) converting said N-Boc-4-hydroxymethyl indole into benzylic bromide,
   h) performing $SN_2$ displacement of the bromide of said benzylic bromide with a carbanion to produce diastereomeric bislactim products,
   i) isolating one of said diastereomeric bislactim products,
   j) hydrolyzing said isolated diastereomeric bislactim product to produce an aminoester product, k) saponifying said aminoester product to produce an N$^{ind}$-t-Boc amino acid, and l) removing the Boc group to produce neo-tryptophan.

16. A method of synthesizing a neo-tryptophan derivative, said method comprising:
   a) providing 4-hydroxymethyl indole, wherein the N-1nitrogen of said 4-hydroxymethyl indole is protected by a protecting group, wherein said protecting group comprises Boc, and
   b) substituting the hydroxyl group of said 4-hydroxymethyl indole with a glycyl unit to produce a neo-tryptophan derivative.

17. A method of synthesizing a neo-tryptophan derivative, said method comprising:
   a) providing 4-hydroxymethyl indole, wherein the N-1nitrogen of said 4-hydroxymethyl indole is protected by a protecting group,
   b) substituting the hydroxyl group of said 4-hydroxymethyl indole with a glycyl unit, and
   c) adding an additional protecting group to the nitrogen within said glycyl unit to produce a neo-tryptophan derivative, wherein said additional protecting group comprises Fmoc.

18. A method of making a polypeptide containing neo-tryptophan, said method comprising:
   a) providing a neo-tryptophan derivative, and
   b) linking an amino acid residue to said neo-tryptophan derivative to form said polypeptide containing neo-tryptophan.

19. The method of claim 18, wherein said neo-tryptophan derivative contains a blocking group attached to a nitrogen atom.

20. The method of claim 18, wherein said neo-tryptophan is L-neo-tryptophan.

21. The method of claim 18, wherein said neo-tryptophan is D-neo-tryptophan.

22. A method of inducing a neurotensin response in a mammal, said method comprising administering an effective dose of a polypeptide to said mammal, wherein said polypeptide comprises neo-tryptophan.

23. The method of claim 22, wherein said mammal is a human.

24. The method of claim 22, wherein said administration is extracranial.

25. The method of claim 22, wherein said administration is an intraperitoneal, intravenous, intradermal, subcutaneous, oral, or nasal administration.

26. The method of claim 22, wherein said response comprises antinociception.

27. The method of claim 22, wherein said response comprises hypothermia.

28. The method of claim 22, wherein said response comprises a reduction in appetite.

29. The method of claim 22, wherein said response comprises a reduction in body weight.

30. The method of claim 22, wherein said response comprises a reduction in body weight gain.

31. The method of claim 22, wherein said response comprises preventing or reducing catalepsy.

32. The method of claim 22, wherein said response comprises reducing an effect of a CNS stimulant.

33. The method of claim 32, wherein said CNS stimulant comprises apomorphine.

34. The method of claim 33, wherein said effect comprises a climbing behavior.

35. The method of claim 32, wherein said CNS stimulant is selected from the group consisting of amphetamine and cocaine.

36. The method of claim 22, wherein said response comprises an antipsychotic effect.

37. The method of claim 36, wherein said polypeptide reduces the signs or symptoms of schizophrenia in said mammal.

38. The method of claim 22, wherein said polypeptide interacts with a neurotensin receptor.

39. The method of claim 38, wherein said neurotensin receptor is a rat neurotensin receptor.

40. The method of claim 38, wherein said neurotensin receptor is a human neurotensin receptor.

41. The method of claim 22, wherein said polypeptide is selected from the group consisting of NT64D, NT64L, NT65L, NT66D, NT66L, NT67L, NT69L, NT69L', NT71, NT72, NT73, NT74, NT75, NT76, and NT77.

42. A method of treating a mammal having a serotonin recognition molecule, said method comprising administering a composition to said mammal, wherein said composition interacts with said sertonin recognition molecule, said composition comprising neo-tryptophan.

43. The method of claim 42, wherein said mammal is a human.

44. The method of claim 42, wherein said composition comprises a polypeptide.

45. The method of claim 42, wherein said serotonin recognition molecule comprises a serotonin receptor.

46. The method of claim 45, wherein said serotonin receptor is a 5HT$_{2A}$ receptor.

47. A method for screening a polypeptide for in vivo use, said method comprising:
   a) contacting a polypeptide with a protease, wherein said polypeptide contains neo-tryptophan, and
   b) determining whether or not said polypeptide remains intact.

48. A composition, wherein said composition comprises neo-tryptophan.

49. The composition of claim 48, wherein said neo-tryptophan is L-neo-tryptophan.

50. The composition of claim 48, wherein said neo-tryptophan is D-neo-tryptophan.

51. A composition, wherein said composition comprises neo-tryptophan having a blocking group, wherein said blocking group comprises Fmoc.

52. A composition, wherein said composition comprises neo-tryptophan having a blocking group, wherein said blocking group comprises Boc.

53. A composition, said composition comprising a compound having the following structure:

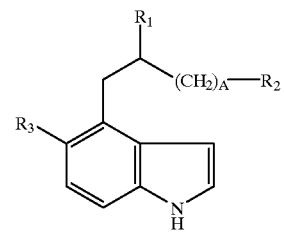

wherein R$_1$ and R$_2$ independently are H, OH, CH$_3$, SH, F, NH$_2$, or COOH, R$_3$ is H, CH$_3$, SH, F, NH$_2$, or COOH, and A is zero.

54. A composition, said composition comprising a compound having the following structure:

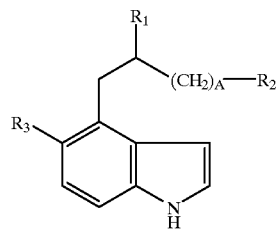

wherein $R_1$ is OH, $CH_3$, SH, F, $NH_2$, or COOH, $R_2$ is OH, SH, or F, $R_3$ is OH, and A is zero.

55. A composition, said composition comprising a compound having the following structure:

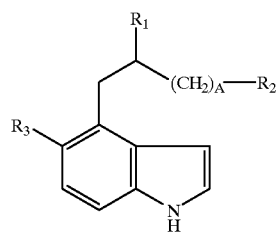

wherein $R_1$ is H, OH, SH, F, $NH_2$, or COOH, $R_2$ is OH, SH, or F, $R_3$ is OH, and A is zero.

56. A composition, said composition comprising a compound having the following structure:

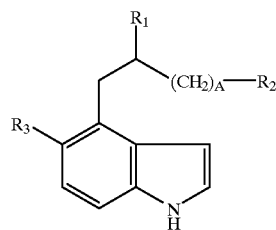

wherein $R_1$ is H, OH, $CH_3$, SH, F, or COOH, $R_2$ is H, OH, $CH_3$, SH, F, or COOH, $R_3$ is OH, and A is zero.

57. A composition, said composition comprising a compound having the following structure:

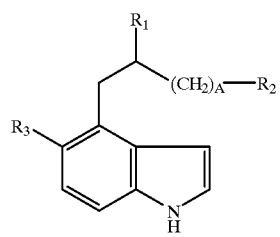

wherein $R_1$ is H, OH, $CH_3$, SH, F, or $NH_2$, $R_2$ is OH, SH, or F, $R_3$ is OH, and A is zero.

58. A method of treating a mammal having a serotonin recognition molecule, said method comprising administering a composition to said mammal, wherein said composition interacts with said serotonin recognition molecule, said composition comprising a compound having the following structure:

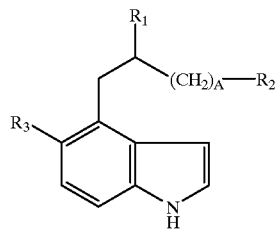

wherein $R_1$, $R_2$, and $R_3$ independently are H, OH, $CH_3$, SH, F, $NH_2$, or COOH, and A is one, two, or three.

59. A method of treating a mammal having a serotonin recognition molecule, said method comprising administering a composition to said mammal, wherein said composition interacts with said serotonin recognition molecule, said composition comprising a compound having the following structure:

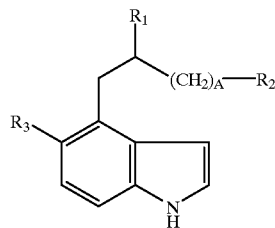

wherein $R_1$ and $R_2$ independently are H, OH, $CH_3$, SH, F, $NH_2$, or COOH, $R_3$ is H, $CH_3$, SH, F, $NH_2$, or COOH, and A is zero.

60. A method of treating a mammal having a serotonin recognition molecule, said method comprising administering a composition to said mammal, wherein said composition interacts with said serotonin recognition molecule, said composition comprising a compound having the following structure:

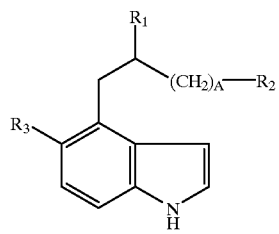

wherein $R_1$ is OH, $CH_3$, SH, F, $NH_2$, or COOH, $R_2$ is OH, SH, or F, $R_3$ is OH, and A is zero.

61. A method of treating a mammal having a serotonin recognition molecule, said method comprising administering a composition to said mammal, wherein said composition interacts with said serotonin recognition molecule, said composition comprising a compound having the following structure:

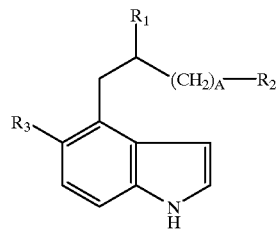

wherein $R_1$ is H, OH, SH, F, $NH_2$, or COOH, $R_2$ is OH, SH, or F, $R_3$ is OH, and A is zero.

62. A method of treating a mammal having a serotonin recognition molecule, said method comprising administering a composition to said mammal, wherein said composition interacts with said serotonin recognition molecule, said composition comprising a compound having the following structure:

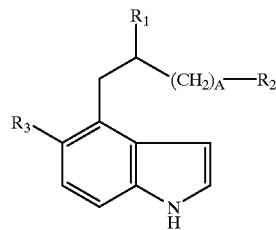

wherein $R_1$ is H, OH, $CH_3$, SH, F, or COOH, $R_2$ is H, OH, $CH_3$, SH, F, or COOH, $R_3$ is OH, and A is zero.

63. A method of treating a mammal having a serotonin recognition molecule, said method comprising administering a composition to said mammal, wherein said composition interacts with said serotonin recognition molecule, said composition comprising a compound having the following structure:

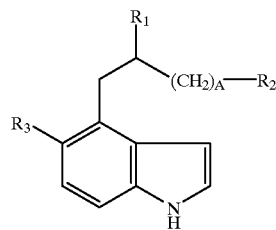

wherein $R_1$ is H, OH, $CH_3$, SH, F, or $NH_2$, $R_2$ is OH, SH, or F, $R_3$ is OH, and A is zero.

64. A composition, said composition comprising a compound having the following structure:

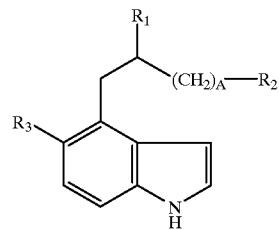

wherein $R_1$ is H, OH, $CH_3$, SH, F, or COOH, $R_2$ is H, OH, $CH_3$, SH, F, $NH_2$ or COOH, $R_3$ is H, OH, $CH_3$, SH, F, $NH_2$ or COOH, and A is one.

65. A composition, said composition comprising a compound having the following structure:

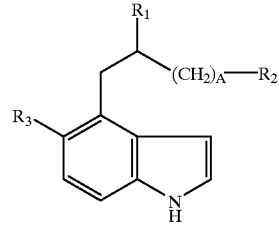

wherein $R_1$ is H, OH, $CH_3$, SH, F, $NH_2$ or COOH, $R_2$ is OH, $CH_3$, SH, F, $NH_2$ or COOH, $R_3$ is H, OH, $CH_3$, SH, F, $NH_2$ or COOH, and A is one.

66. A composition, said composition comprising a compound having the following structure:

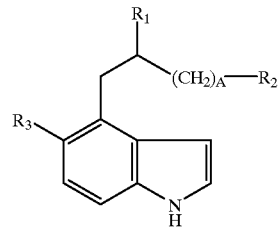

wherein $R_1$ is H, OH, $CH_3$, SH, F, $NH_2$ or COOH, $R_2$ is H, OH, $CH_3$, SH, F, $NH_2$ or COOH, $R_3$ is H, $CH_3$, SH, F, $NH_2$ or COOH, and A is one.

* * * * *